(12) United States Patent
Bryant et al.

(10) Patent No.: US 7,084,142 B2
(45) Date of Patent: *Aug. 1, 2006

(54) PLATELET ADENOSINE DIPHOSPHATE RECEPTOR ANTAGONISTS

(75) Inventors: Judi Bryant, Mill Valley, CA (US); Brad Buckman, Oakland, CA (US); Imadul Islam, Hercules, CA (US); Raju Mohan, Encinitas, CA (US); Michael Morrissey, Danville, CA (US); Guo Ping Wei, San Ramon, CA (US); Wei Xu, Danville, CA (US); Shendong Yuan, Richmond, CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/331,621

(22) Filed: Jan. 12, 2006

(65) Prior Publication Data

US 2006/0122188 A1    Jun. 8, 2006

Related U.S. Application Data

(63) Continuation of application No. 10/731,815, filed on Dec. 9, 2003.

(60) Provisional application No. 60/432,792, filed on Dec. 11, 2002.

(51) Int. Cl.
*A61K 31/496*     (2006.01)
*C07D 401/12*     (2006.01)

(52) U.S. Cl. .................. 514/253.06; 544/363

(58) Field of Classification Search ........... 544/363; 514/253.06

See application file for complete search history.

(56) References Cited

U.S. PATENT DOCUMENTS

| 6,861,424 B1 * | 3/2005 | Bryant et al. ............ 514/235.2 |
| 2003/0060474 A1 | 3/2003 | Bryant et al. |

FOREIGN PATENT DOCUMENTS

| EP | 739 886 A2 | 10/1996 |
| GB | 1334705 | 10/1973 |
| WO | WO 92/08709 | 5/1992 |
| WO | WO 98/56771 | 12/1998 |

OTHER PUBLICATIONS

Dullweber, F. et al., "Factorising Ligand Affinity: A Combined Thermodynamic and Crystallographic Study of Trypsin and Thrombin Inhibition," *J. Mol Biol.* 313: 593-614, 2001.

Folts et al., "Platelet Aggregation in Partially Obstructed Vessels and its Elimination with Asprin," *Circulation* 54(3):365-370, 1976.

Gachet et al., "Purinoceptors on Blood Platelets: Further Pharmaceutical and Clinical Evidence to Suggest the Presence of Two ADP Receptors," *British Journal Haematology.* 91(2): 434-444, Oct. 1995.

Herbert et al., "Clopidogrel, A Novel Antiplatelet and Antithrombotic Agent," *Cardiovascular Drug reviews* 11(2): 180-198, 1993.

Humphries et al., "Pharmacological Profile of the Novel P2T-Purinoceptor Antagonist, FPL 67085 in vitro and in the Anaesthrtized Rat in vivo," *British Journal of Pharmacology.* 115(6): 1110-1116, Jul. 1995.

Kamm, W. et al., "Transport of Peptidomimetic Thrombin Inhibitors with 3-Amidino-Phyenylalanine Structure: Permeability and Efflux Mechanism in Monolayers of a Human Intestinal Cell Line (Caco-2)," *Pharmaceutical Research* 18(8): 1110-1118, 2001.

Kaslow and Marsh, "Substituted Bromoquinolines" *J. Organic Chemistry* 12(3):456-458, May 1947.

Mills, "ADP Receptor on Platelets," *Thrombosis Haemostasis* 76(6):835-856, Dec. 1996.

Mustard et al., "Isolation of Human Platelets from Plasma by Centrifugation and Washing." *Methods Enzymology* 169:3-11, 1989.

Pierce, A.C. and Jorgensen, W.L., "Estimation of Binding Affinities for Selecti e Thrombin Inhibitors via Monte Carlo Simulations," *J. Med. Chem.* 44: 1043-1050, 2001.

Spath, "Zur Konstitution der Kynurensaure," *Monatshefte fur Chimie* 42: 89-95, 1921.

Cornish, J. et al., "Trifuoroacetate, a Contaminant in Purified Proteins, Inhibits Proliferation of Osteoblasts and Chondrocytes," *Am J Pysiol Endocrinol Metab, 277: E779-E783,* 1999.

* cited by examiner

Primary Examiner—Emily Bernhardt
(74) Attorney, Agent, or Firm—Jacqueline S. Larson; Wendy L. Washtien

(57) ABSTRACT

Compounds of the following formula:

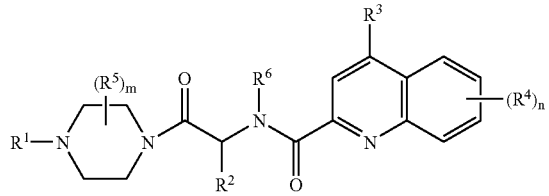

where m, n, $R^1$, $R^2$, $R^3$, $R^4$ and $R^6$ are described herein, are useful as inhibitors of platelet adenosine diphosphate. Pharmaceutical compositions containing these compounds, methods of using these compounds as antithrombotic agents and processes for synthesizing these compounds are also described herein.

15 Claims, No Drawings

PLATELET ADENOSINE DIPHOSPHATE RECEPTOR ANTAGONISTS

This application is a continuation of U.S. Ser. No. 10/731,815, filed Dec. 9, 2003, now allowed, which claims priority to U.S. Provisional Application Ser. No. 60/432,792, filed Dec. 11, 2002, the entire disclosures of which are incorporated herein by reference.

FIELD OF THE INVENTION

The invention relates to quinoline derivatives, their use as platelet adenosine diphosphate receptor antagonists, compositions containing them and processes for their preparation.

BACKGROUND OF THE INVENTION

Platelets interact with the coagulation and fibrinolysis systems in the maintenance of hemostasis and in the pathogenesis of thrombosis and thromboembolism. Platelets rapidly adhere to damaged vascular tissue, and release a variety of prothrombotic, chemotactic, and mitogenic factors, aimed at prompting hemostasis and wound healing. Platelets also play an important role in arterial thrombosis, a common cause of death and disability in patients with cardiovascular disease. Platelet inhibitors have been successfully used for secondary prevention of arterial thrombosis in patients with coronary, cerebral, and peripheral vascular disease.

Platelets adhere to exposed subendothelium after vessel wall injury by binding to von Willebrand factor (vWf) and collagen. This induces platelets to change shape from a disc shape to a round form with pseudopodia, which enforces platelet adhesion and aggregation. The final common pathway for platelet aggregation is the activation of the fibrinogen receptor (GPIIb-IIIa). As a result, dimeric fibrinogen molecules present in plasma can bind and link platelets together to form aggregates.

Activated platelets secrete their granule contents, many of which act directly on blood cells, including platelets themselves, and endothelium. Platelets contain several kinds of secretory granules. The dense-granules contain adenosine diphosphate ("ADP"), adenosine triphosphate ("ATP") and serotonin. The α-granules contain several platelet-specific proteins (platelet factor 4 and β-thromboglobulin), growth factors (PDGF, TGF-β, EGF and ECGF) and coagulation factors (fibrinogen, Factor V and vWf). Platelets also secrete biologically active arachidonic acid products. Well known is $TxA_2$ which is inhibited by aspirin through irreversible inactivation of the cyclooxygenase producing $TxA_2$.

Many stimuli, such as thrombin, collagen, ADP and thromboxane A2 ($TxA_2$), activate platelets by binding to their cell surface receptors. Most of these receptors are G-protein-coupled receptors. Activation of G-proteins has been shown to be an essential event in platelet activation. For example, platelets from Gq-/- mice do not aggregate in response to thrombin, collagen, ADP or $TxA_2$ (Offermans, S. et al., Nature (1998), Vol. 389, No. 11, pp. 183–185). Many down-stream signaling events have been elucidated, including activation of phospholipase-C (PLC) and protein kinase C, increase in intracellular calcium concentration, decrease in cAMP level and tyrosine phosphorylation.

ADP plays a pivotal role in platelet activation. ADP not only causes primary aggregation of platelets but is also responsible for the secondary aggregation following activation by other agonists such as thrombin and collagen. Contained at very high concentrations in the platelet dense-granules, ADP is released when platelets are activated to reinforce platelet aggregation.

ADP-induced platelet activation plays an important role in maintaining normal hemostasis. Several congenital bleeding disorders have been linked to the decreased number of platelet ADP receptors and deficiency of ADP-induced platelet aggregation. Patients having "storage pool disease", which is due to defects in the storage of nucleotides and/or their secretion from the platelet dense-granules, have impaired platelet aggregation in response to collagen and other stimuli due to the absence of the amplification effects by ADP.

ADP-induced platelet activation also plays a key role in the initiation and propagation of thrombosis. Administration of ADP has been shown to induce thrombus formation in rat and mice mesenteric venules. In contrast, ADP-removing enzymes have been shown to dramatically reduce platelet deposition on collagen and to inhibit laser-induced thrombosis in rat mesenteric arterioles and venules, supporting the theory that ADP plays a role in mediating platelet recruitment in thrombus formation. Several ADP-induced early signaling events in platelets have been described. These include a transient rise in free cytoplasmic calcium, an inhibition of adenylate cyclase through activation of $G_{i2}$, an increase in cytosolic pH by activating the Na+/H+-exchange, and exposure of the platelet binding sites for fibrinogen independent of protein kinase C. While these signaling events collectively contribute to platelet aggregation, the specific role of each remains the subject of on-going investigations.

The current model of ADP-induced platelet activation involves two G-protein coupled purinergic receptors, one of which is coupled to the activation of the phospholipase-C pathway ($P2Y_1$) and the other is coupled to the inhibition of adenylate cyclase ($P2Y_{AC}$). $P2Y_{AC}$ is the best target for a platelet ADP receptor antagonist for several reasons. First, $P2Y_{AC}$ is predominately platelet specific. Secondly, it is required for ADP-induced aggregation. Thirdly, it plays an important role in sustaining thrombin or collagen-induced aggregation. Finally, it is the molecular target for anti-aggregatory drugs such as Clopidogrel and Ticlopidine. Both of these drugs have been shown to be efficacious in various thrombosis models. However, Clopidogrel has been shown to be an irreversible inhibitor of platelet aggregation with a slow onset of action. Similarly, the ATP analogues, AR-C67085 and AR-C69931MX, which are potent antagonists for ADP-induced platelet aggregation, have also been shown to be effective in thrombosis models and are currently under clinical investigation. All these findings indicate that ADP is a critical mediator of arterial thrombus formation and hence an excellent target for antithrombotic intervention.

When the properties of current oral platelet inhibitors, such as aspirin, Clopidogrel and Ticlopidine are compared, it becomes clear that, while relatively safe, current oral platelet inhibitors are only modestly effective in preventing thrombotic complications in patients with underlying vascular disease. It is clear that there is a need in this field for a potent, selective, reversible, orally active platelet ADP receptor ($P2Y_{AC}$) inhibitor.

SUMMARY OF THE INVENTION

The compounds of the invention are antagonists of the platelet ADP receptor, $P2Y_{AC}$, and are therefore useful in treating disease-states characterized by thrombotic activity and in so doing are useful as antithrombotic agents in the treatment and prevention of thrombosis. Accordingly, in one aspect, the invention is directed to compounds selected from the group consisting of the following formula (I):

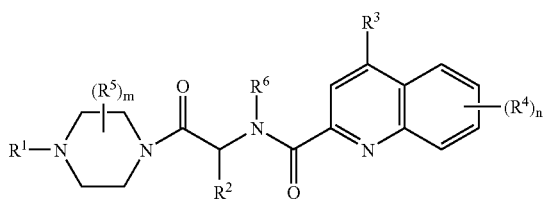
(I)

wherein:

m and n are independently 1 to 4;

$R^1$ is hydrogen, alkyl, carboxyalkyl, aryl, aralkyl, alkylcarbonyl, aryloxyalkylcarbonyl, carboxyalkylcarbonyl, alkoxycarbonylalkylcarbonyl, alkoxycarbonylalkyl, alkoxycarbonyl, arylcarbonyl, aryloxycarbonyl, aralkoxycarbonyl, cycloalkylcarbonyl, haloalkoxycarbonyl, aminocarbonyl, monoalkylaminocarbonyl, dialkylaminocarbonyl, alkoxycarbonylaminocarbonyl, or heterocyclylcarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, or heterocyclylalkyl;

$R^3$ is aryl or aryloxy each independently optionally substituted by one or more substituents selected from the group consisting of alkyl, halo, haloalkyl, cyano, nitro, tetrazolyl, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;

or $R^3$ is aralkyl or aralkoxy, wherein the alkyl radical in the aralkyl or aralkoxy substituent is optionally substituted by one or more substituents selected from the group consisting of halo, cyano, nitro, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, and $-R^9-N(R^7)C(O)OR^9$), and wherein the aryl radical in the aralkyl or aralkoxy substituent is independently optionally substituted by one or more substituents selected from the group consisting of alkyl, halo, haloalkyl, cyano, nitro, tetrazolyl, $-R^8-OR^7$, $-R^8-C(O)R^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^6$ is hydrogen, alkyl, carboxyalkyl, or alkoxycarbonylalkyl;

each $R^7$ is hydrogen, alkyl, aryl, aralkyl; or haloalkyl;

each $R^8$ is a bond or a straight or branched alkylene chain; and each $R^9$ is hydrogen, alkyl, aralkyl or haloalkyl;

as a single stereoisomer, a mixture of individual stereoisomers, or a racemic mixture;

or a pharmaceutically acceptable salt thereof.

In another aspect, this invention is compounds selected from the group consisting of the following formula (II):

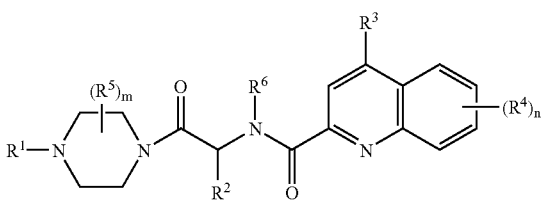
(II)

wherein:

m and n are independently 1 to 4;

$R^1$ is hydrogen, alkyl, carboxyalkyl, aryl, aralkyl, alkylcarbonyl, aryloxyalkylcarbonyl, carboxyalkylcarbonyl, alkoxycarbonylalkylcarbonyl, alkoxycarbonylalkyl, alkoxycarbonyl, arylcarbonyl, aryloxycarbonyl, aralkoxycarbonyl, cycloalkylcarbonyl, haloalkoxycarbonyl, aminocarbonyl, monoalkylaminocarbonyl, dialkylaminocarbonyl, alkoxycarbonylaminocarbonyl, or heterocyclylcarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, or heterocyclylalkyl;

$R^3$ is heteroaryl optionally substituted by one or more substituents selected from the group consisting of alkyl, halo, haloalkyl, cyano, nitro, tetrazolyl, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;

or $R^3$ is heteroarylalkoxy, wherein the alkoxy radical in the heteroarylalkoxy substituent is optionally substituted by one or more substituents selected from the group consisting of halo, cyano, nitro, $-R^8-OR^7$, $-R^8-C(O)OR^7$, $-R-C(O)N(R^7)_2$, $-R-C(O)R^7$, $-R^8-N(R^7)_2$, $-R^8-N(R^7)C(O)R^7$, and $-R^9-N(R^7)C(O)OR^9$), and wherein the heteroaryl radical in the heteroarylalkoxy substituent is independently optionally substituted by one or more substituents selected from the group consisting of alkyl, halo, haloalkyl, cyano, nitro, tetrazolyl $-R^8-$ OR$^7$, —R$^8$—C(O)OR$^7$, —R$^8$—C(O)N(R$^7$)$_2$, —R$^8$—C(O)R$^7$, —R$^8$—N(R$^7$)$_2$, —R$^8$—N(R$^7$)C(O)R$^7$, —R$^8$—N(R$^7$)C(O)OR$^9$, —R$^8$—N(R$^7$)—S(O)$_2$—R$^7$, and —R$^8$—C[N(R$^7$)$_2$]—C(O)OR$^7$;

each R$^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each R$^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

R$^6$ is hydrogen, alkyl, carboxyalkyl, or alkoxycarbonylalkyl;

each R$^7$ is hydrogen, alkyl, aryl, aralkyl, or haloalkyl;

each R$^8$ is a bond or a straight or branched alkylene chain; and each R$^9$ is hydrogen, alkyl, aralkyl or haloalkyl;

as a single stereoisomer, a mixture of individual stereoisomers, or a racemic mixture;

or a pharmaceutically acceptable salt thereof.

In another aspect, this invention is directed to pharmaceutical compositions useful in treating a mammal having a disease-state characterized by thrombotic activity, which composition comprises a pharmaceutically acceptable excipient and a compound of formula (I) or a compound of formula (II) as defined above.

In another aspect, this invention is directed to methods of treating disease-states characterized by thrombotic activity, which methods comprise administering to a mammal having a disease-state characterized by thrombotic activity a therapeutically effective amount of a compound of formula (I) or formula (II) as defined above.

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like. Unless stated otherwise specifically in the specification, it is understood that for radicals, as defined below, that contain a substituted alkyl group that the substitution can occur on any carbon of the alkyl group.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like.

"Alkylcarbonyl" refers to a radical of the formula —C(O)—R$_a$ where R$_a$ is an alkyl radical as defined above, e.g., acetyl, ethylcarbonyl, n-propylcarbonyl, and the like.

"Alkylcarbonylamino" refers to a radical of the formula —N(H)—C(O)—R$_a$ where R$_a$ is an alkyl radical as defined above, e.g., acetylamino, ethylcarbonylamino, n-propylcarbonylamino, and the like.

"Alkylthio" refers to a radical of the formula —S—R$_a$ where R$_a$ is an alkyl radical as defined above, e.g., methylthio, ethylthio, n-propylthio, and the like.

"Alkylsulfonylalkyl" refers to a radical of the formula —R$_a$—S(O)$_2$—R$_a$ where each R$_a$ is independently an alkyl radical as defined above, e.g., methylsulfonylmethyl, 2-methylsulfonylethyl, 2-ethylsulfonylpropyl, and the like.

"Alkoxy" refers to a radical of the formula —OR$_a$ where R$_a$ is an alkyl radical as defined above, e.g., methoxy, ethoxy, n-propoxy, 1-methylethoxy (isopropoxy), n-butoxy, n-pentoxy, 1,1-dimethylethoxy (t-butoxy), and the like.

"Alkoxycarbonyl" refers to a radical of the formula —C(O)OR$_a$ where R$_a$ is an alkyl radical as defined above, e.g., methoxycarbonyl, ethoxycarbonyl, n-propoxycarbonyl, and the like.

"Alkoxycarbonylalkyl" refers to a radical of the formula —R$_a$—C(O)OR$_a$ where each R$_a$ is independently an alkyl radical as defined above, e.g., methoxycarbonylmethyl, (1,1-dimethylethoxy)carbonylmethyl, 2-(methoxycarbonyl)ethyl, and the like.

"Alkoxycarbonylaminocarbonyl" refers to a radical of the formula —C(O)—N(H)—C(O)OR$_a$ where R$_a$ is an alkyl radical as defined above, e.g., methoxycarbonylaminocarbonyl, ethoxycarbonylaminocarbonyl, n-propoxycarbonylaminocarbonyl, and the like.

"Alkoxyalkoxyalkylcarbonyl" refers to a radical of the formula —C(O)—R$_a$—O—R$_a$—O—R$_a$ where each R$_a$ is independently an alkyl radical as defined above, e.g., 2-(ethoxy)ethoxymethylcarbonyl, 3-(2-(n-butoxy)ethoxy)propylcarbonyl, and the like.

"Alkoxycarbonylalkyl" refers to a radical of the formula —R$_a$—C(O)OR$_a$ where each R$_a$ is independently an alkyl radical as defined above, e.g., methoxycarbonylmethyl, 2-(ethoxycarbonyl)ethyl, 2-(methoxycarbonyl)propyl, and the like.

"Alkoxycarbonylalkoxy" refers to a radical of the formula —O—R$_a$—C(O)OR$_a$ where each R$_a$ is independently an alkyl radical as defined above, e.g., methoxycarbonylmethoxy, 2-(ethoxycarbonyl)ethoxy, 2-(methoxycarbonyl)propoxy, and the like.

"Alkoxycarbonylalkylcarbonyl" refers to a radical of the formula —C(O)—R$_a$—C(O)OR$_a$ where each R$_a$ is independently an alkyl radical as defined above, e.g., methoxycarbonylmethylcarbonyl, 2-(ethoxycarbonyl)ethylcarbonyl, 2-(methoxycarbonyl)propylcarbonyl, and the like.

"Alkoxycarbonylalkylaminocarbonylalkyl" refers to a radical of the formula —R$_a$—C(O)—N(H)—R$_a$—C(O)OR$_a$ where each R$_a$ is independently an alkyl radical as defined above, e.g., methoxycarbonylmethyl, 2-(ethoxycarbonyl)ethylaminocarbonylmethyl, 2-(2-(methoxycarbonyl)propylaminocarbonyl)propyl, and the like.

"Alkoxycarbonylalkylthioalkyl" refers to a radical of the formula —R$_a$—S—R$_a$—C(O)OR$_a$ where each R$_a$ is independently an alkyl radical as defined above, e.g., methoxycarbonylmethylthiomethyl, 2-(ethoxycarbonyl)ethylthiomethyl, 2-(2-(methoxycarbonyl)propylthio)propyl, and the like.

"Alkoxycarbonylalkoxycarbonylalkyl" refers to a radical of the formula —R$_a$—C(O)—O—R$_a$—C(O)OR$_a$ where each R$_a$ is independently an alkyl radical as defined above, e.g., methoxycarbonylmethoxy, 2-(ethoxycarbonyl)ethoxycarbonylmethyl, 3-(2-(methoxycarbonyl)propoxycarbonyl)propyl, and the like.

"(Alkoxycarbonylalkyl)(alkyl)aminocarbonylalkyl" refers to a radical of the formula —R$_a$—C(O)—N(R$_a$)—R$_a$—C(O)OR$_a$ where each R$_a$ is independently an alkyl radical as defined above, e.g., (methoxycarbonylmethyl)

(methyl)aminocarbonylmethyl, 2-((ethoxycarbonylmethyl)(methyl)aminocarbonyl)ethyl, and the like.

"Amino" refers to the —$NH_2$ radical.

"Aminoalkyl" refers to a radical of the formula —$R_a$—$NH_2$, e.g., aminomethyl, 2-aminomethyl, 2-aminopropyl, and the like.

"Aminocarbonyl" refers to the —C(O)$NH_2$ radical.

"Aminocarbonylalkoxy" refers to a radical of the formula —O—$R_a$—C(O)$NH_2$, e.g., aminocarbonylmethoxy, 2-(aminocarbonyl)ethoxy, 2-(aminocarbonyl)propoxy, and the like.

"Aminocarbonylalkyl" refers to a radical of the formula —$R_a$—C(O)$NH_2$, e.g., aminocarbonylmethyl, 2-(aminocarbonyl)ethyl, 2-(aminocarbonyl)propyl, and the like.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, halo, haloalkyl, cyano, nitro, tetrazolyl, —$R^8$—$OR^7$, —$R^8$—C(O)$OR^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N($R^7$)C(O)$OR^9$, —$R^8$—N($R^7$)—S(O)$_2$—$R^7$, —$R^8$—C[N($R^7$)$_2$]—C(O)$OR^7$, wherein each $R^7$ is hydrogen, alkyl, aryl, aralkyl, or haloalkyl, each $R^8$ is a bond or a straight or branched alkylene chain, and each $R^9$ is hydrogen, alkyl, aralkyl or haloalkyl as defined herein.

"Aralkyl" refers to a radical of the formula —$R_a R_b$ where $R_a$ is an alkyl radical as defined above, substituted by $R_b$, an aryl radical, as defined above, e.g., benzyl. The $R_a$ radical may be optionally substituted by one or more substituents selected from the group consisting of halo, cyano, nitro, —$R^8$—$OR^7$, —$R^8$—C(O)$OR^7$, —$R^8$—C(O)N($R^7$)$_2$, —$R^8$—C(O)$R^7$, —$R^8$—N($R^7$)$_2$, —$R^8$—N($R^7$)C(O)$R^7$, and —$R^9$—N($R^7$)C(O)$OR^9$, wherein each $R^7$ is hydrogen, alkyl, aryl, aralkyl, or haloalkyl, each $R^8$ is a bond or a straight or branched alkylene chain, and each $R^9$ is hydrogen, alkyl, aralkyl or haloalkyl as defined herein. The $R_b$ radical may be optionally substituted one or more substituents selected from the group consisting of alkyl, halo, haloalkyl, cyano, nitro, tetrazolyl, —$R^8$—$OR^7$, —$R^8$—C(O)$OR^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N($R^7$)C(O)$OR^9$, —$R^8$—N($R^7$)—S(O)$_2$—$R^7$, —$R^8$—C[N($R^7$)$_2$]—C(O)$OR^7$, wherein each $R^7$ is hydrogen, alkyl, aryl, aralkyl, or haloalkyl, each $R^8$ is a bond or a straight or branched alkylene chain, and each $R^9$ is hydrogen, alkyl, aralkyl or haloalkyl as defined herein.

"Aryloxy" refers to a radical of the formula —$OR_b$ where $R_b$ is an optionally substituted aryl radical as defined above, e.g., phenoxy.

"Arylcarbonyl" refers to a radical of the formula —C(O)—$R_b$ where $R_b$ is an optionally substituted aryl radical as defined above, e.g., phenylcarbonyl, (4-acetylaminophenyl)carbonyl, (2-methoxyphenyl)carbonyl, and the like. For $R^1$, preferred arylcarbonyl radicals are those radicals wherein the $R_b$ group is optionally substituted by by one or more substituents independently selected from the group consisting of acetylamino, carboxy, aminocarbonyl, alkoxycarbonyl, haloalkoxy, alkoxy, and alkyl.

"Aryloxycarbonyl" refers to a radical of the formula —C(O)$OR_b$ where $R_b$ is an optionally substituted aryl radical as defined above, e.g., phenoxycarbonyl.

"Aryloxyalkylcarbonyl" refers to a radical of the formula —C(O)$OR_b R_a$ where $R_a$ is an alkyl radical, as defined above, substituted by $R_b$, an optionally substituted aryl radical, as defined above, e.g., phenoxymethylcarbonyl, (2-phenoxyethyl)carbonyl, and the like.

"Aralkoxy" refers to a radical of the formula —$OR_e$ where $R_e$ is an optionally substituted aralkyl radical as defined above, e.g., benzyloxy, 3-phenylpropoxy, and the like.

"Aralkoxyalkyl" refers to a radical of the formula —$R_a$—$OR_e$ where $R_a$ is an alkyl radical as defined above and $R_e^a$ is an optionally substituted aralkyl radical as defined above, e.g., benzyloxymethyl, 2-(benzyloxy)ethyl, 2-(benzyloxy)propyl, and the like.

"Aralkoxycarbonyl" refers to a radical of the formula —C(O)$OR_e$ where $R_e$ is an optionally substituted aralkyl radical as defined above, e.g., benzyloxycarbonyl, and the like.

"Aralkoxycarbonylalkyl" refers to a radical of the formula —$R_a$—C(O)$OR_e$ where $R_a$ is an alkyl radical as defined above and Re is an optionally substituted aralkyl radical as defined above, e.g., benzyloxycarbonylmethyl, 2-(benzyloxycarbonyl)ethyl, 3-((naphthalen-2-yl)oxy)carbonyl)propyl, and the like.

"Aralkoxycarbonylaminoalkyl" refers to a radical of the formula —$R_a$—N(H)—C(O)$OR_e$ where $R_a$ is an alkyl radical as defined above and $R_e$ is an optionally substituted aralkyl radical as defined above, e.g., benzyloxycarbonylaminomethyl, 2-(benzyloxycarbonylamino)ethyl, 2-(benzyloxycarbonylamino)propyl, and the like.

"Carboxy" refers to the —C(O)OH radical.

"Carboxyalkyl" refers to a radical of the formula —$R_a$—C(O)OH, where $R_a$ is an alkyl radical as defined above, e.g., carboxymethyl, 2-carboxyethyl, 2-carboxypropyl and the like.

"Carboxyalkoxy" refers to a radical of the formula —O—$R_a$—C(O)OH, where $R_a$ is an alkyl radical as defined above, e.g., carboxymethoxy, 2-carboxyethoxy, 2-carboxypropoxy, and the like.

"Carboxyalkylcarbonyl" refers to a radical of the formula —C(O)—$R_a$—C(O)OH, where $R_a$ is an alkyl radical as defined above, e.g., 2-carboxyethylcarbonyl, carboxymethylcarbonyl, 3-carboxypropylcarbonyl, and the like.

"Carboxyalkylamino" refers to a radical of the formula —N(H)—$R_a$—C(O)OH where $R_a$ is an alkyl radical as defined above, e.g., carboxymethylamino, 2-carboxyethylamino, 3-carboxypropylamino, and the like.

"Carboxyalkylaminocarbonylalkyl" refers to a radical of the formula —$R_a$—C(O)—N(H)—$R_a$—C(O)OH where each $R_a$ is independently an alkyl radical as defined above, e.g., carboxymethylaminocarbonylmethyl, 2-(carboxymethylaminocarbonyl)ethyl, 2-(2-carboxyethyl)aminocarbonyl)ethyl, 3-(2-carboxyethyl)aminocarbonyl)butyl, and the like.

"Carboxyalkylthioalkyl" refers to a radical of the formula —$R_a$—S—$R_a$—C(O)OH were each $R_a$ is independently an alkyl radical as defined above, e.g., carboxymethylthiomethyl, (1-carboxyethyl)thiomethyl, 2-((1-carboxypropyl)thio)ethyl, and the like.

"Carboxyalkoxyalkyl" refers to a radical of the formula —$R_a$—O—$R_a$—C(O)OH where each $R_a$ is independently an alkyl radical as defined above, e.g., 2-(carboxymethoxy)ethyl, (2-carboxyethoxy)methyl, 3-(2-carboxypropoxy)propyl, and the like.

"Carboxyalkoxycarbonylalkyl" refers to a radical of the formula —$R_a$—C(O)—O—$R_a$—C(O)OH where each $R_a$ is independently an alkyl radical as defined above, e.g., carboxymethoxycarbonylmethyl, 2-(carboxymethoxycarbonyl)ethyl, 2-((2-carboxyethoxy)carbonyl)propyl, and the like.

"Cycloalkyl" refers to a stable 3- to 10-membered monocyclic or bicyclic radical which is saturated, and which consist solely of carbon and hydrogen atoms, e.g., cyclopropyl, cyclobutyl, cyclobutyl, cyclohexyl, decalinyl and the like. Unless otherwise stated specifically in the specification, the term "cycloalkyl" is meant to include cycloalkyl radicals which are optionally substituted one or more substituents selected from the group consisting of alkyl, halo, haloalkyl, cyano, nitro, tetrazolyl, —$R^8$—$OR^7$, —$R^8$—$C(O)OR^7$, —$R^8$—$C(O)N(R^7)_2$, —$R^8$—$C(O)R^7$, —$R^8$—$N(R^7)_2$, —$R^8$—$N(R^7)C(O)R^7$, —$R^8$—$N(R^7)C(O)OR^9$, —$R^8$—$N(R^7)$—$S(O)_2$—$R^7$, —$R^8$—$C[N(R^7)_2]$—$C(O)OR^7$, wherein each $R^7$ is hydrogen, alkyl, aryl, aralkyl, or haloalkyl, each $R^8$ is a bond or a straight or branched alkylene chain, and each $R^9$ is hydrogen, alkyl, aralkyl or haloalkyl as defined herein.

"Cycloalkylcarbonyl" refers to a radical of the formula —C(O)—$R_c$ where $R_c$ is a cycloalkyl radical as defined above, e.g., cyclobutylcarbonyl, cyclopropylcarbonyl, and the like. For $R^1$, a preferred cycloalkylcarbonyl radical is that radical wherein the $R_c$ group is optionally substituted by a phenyl group.

"(Carboxy)(hydroxy)alkyl" refers to a radical of the formula —$R_a$(OH)—C(O)OH wherein $R_a$ is an alkyl radical defined above substituted by an hydroxy radical and a carboxy radical, as defined herein, e.g., 1-carboxy-3-hydroxypropyl, 2-carboxy-4-hydroxybutyl, 1-carboxy-5-hydroxypent-2-yl, and the like.

"(Carboxyalkyl)(alkyl)aminocarbonylalkyl" refers to a radical of the formula —$R_a$—C(O)—N($R_a$)—$R_a$—C(O)OH wherein each $R_a$ is independently an alkyl radical as defined above, and wherein the nitrogen atom is substituted by the $R_a$ group and the —$R_a$—C(O)OH group, e.g., (carboxyethyl)(ethyl)aminocarbonylmethyl, 2-((2-carboxyethyl)(methyl)aminocarbonyl)ethyl, and the like.

"Cyano" refers to the —C≡N radical.

"Dialkylamino" refers to a radical of the formula —N($R_a$)—$R_a$ where each $R_a$ is independently an alkyl radical, e.g., dimethylamino, diethylamino, methylethylamino, and the like.

"Dialkylaminocarbonyl" refers to a radical of the formula —C(O)—N($R_a$)—$R_a$ where each $R_a$ is independently an alkyl radical, e.g., dimethylaminocarbonyl, diethylaminocarbonyl, methyl(ethyl)aminocarbonyl, and the like.

"Dialkylaminoalkyl" refers to a radical of the formula —$R_a$—N($R_a$)—$R_a$ where each $R_a$ is independently an alkyl radical as defined above, e.g., dimethylaminomethyl, 2-(diethylamino)ethyl, 3-(methyl(ethyl)amino)propyl, and the like.

"Dialkylaminoalkoxy" refers to a radical of the formula —O—$R_a$—N($R_a$)—$R_a$ where each $R_a$ is independently an alkyl radical as defined above, e.g., dimethylaminomethoxy, 2-(diethylamino)ethoxy, 3-(methyl(ethyl)amino)propoxy, and the like.

"Di(alkylcarbonyl)amino" refers to a radical of the formula —N(C(O)—$R_a$)—C(O)—$R_a$ where each $R_a$ is independently an alkyl radical as defined above, e.g., di(acetyl)amino, di(ethylcarbonyl)amino, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkylsulfonylaminoalkyl" refers to a radical of the formula —$R_a$—N(H)—S(O)$_2R_f$ where $R_a$ is an alkyl radical as defined above and $R_f$ is a haloalkyl radical as defined above, e.g., 2-(trifluoromethoxysulfonylamino)ethyl, 3-(trifluoromethoxysulfonylamino)propyl, and the like.

"Haloalkoxy" refers to a radical of the formula —$OR_f$ where $R_f$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Haloalkenyloxy" refers to a radical of the formula —$OR^g$ where $R^g$ is an haloalkenyl radical as defined above, as defined above, e.g., 1,2-difluoroethenyloxy, 3-bromo-2-fluoroprop-1-enyloxy, 1,2-dibromoethenyloxy, and the like.

"Haloalkoxycarbonyl" refers to a radical of the formula —C(O)$OR_f$ where $R_f$ is an haloalkyl radical as defined above, e.g., trifluoromethoxycarbonyl, difluoromethoxycarbonyl, trichloromethoxycarbonyl, 2,2,2-trifluoroethoxycarbonyl, 1-fluoromethyl-2-fluoroethoxycarbonyl, 3-bromo-2-fluoropropoxycarbonyl, 1-bromomethyl-2-bromoethoxycarbonyl, and the like.

"Hydroxy" refers to the —OH radical.

"Hydroxyalkyl" refers to a alkyl radical as defined above that is substituted by a hydroxy radical, e.g., hydroxymethyl, 2-hydroxyethyl, 2-hydroxypropyl, 3-hydroxypropyl, 4-hydroxybutyl, 3-hydroxybutyl, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may be attached to the main structure at any heteroatom or carbon atom which results in the creation of a stable compound. Examples of such heterocyclyl radicals include, but are not limited to, azepinyl, acridinyl, benzimidazolyl, benzthiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, isoindolyl, indolinyl, isoindolinyl, indanyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted one or more substituents selected from the group consisting of alkyl, halo, haloalkyl, cyano, nitro, tetrazolyl, —$R^8$—$OR^7$, —$R^8$—$C(O)OR^7$, —$R^8$—$C(O)N(R^7)_2$, —$R^8$—$C(O)R^7$, —$R^8$—$N(R^7)_2$, —$R^8$—$N(R^7)C(O)R^7$, —$R^8$—$N(R^7)C(O)OR^9$, —$R^8$—$N(R^7)$—$S(O)_2$—$R^7$, —$R^8$—$C[N(R^7)_2]$—$C(O)OR^7$, wherein each $R^7$ is hydrogen, alkyl, aryl, aralkyl, or haloalkyl, each $R^8$ is a bond or a straight or branched alkylene chain, and each $R^9$ is hydrogen, alkyl, aralkyl or haloalkyl as defined herein.

"Heteroaryl" refers to a heterocyclyl radical as defined above wherein the heterocyclyl radical is partially or fully aromatic.

"Heterocyclylalkyl" refers to a radical of the formula —$R_a$—$R_h$ where $R_a$ is an alkyl radical as defined above and Rh is an heterocyclyl radical as defined above, e.g., imidazol-3-ylmethyl, triazol-3-ylmethyl, 2-tetrazolylethyl, and the like. For $R^2$, preferred heterocyclylalkylradicals are those radicals where Rh is selected from the group consisting of imidazolyl (optionally substituted by carboxyalkyl), indolyl, triazolyl and tetrazolyl.

"Heterocyclylalkoxy" refers to a radical of the formula —O—$R_a$—$R_h$ where $R_a$ is an alkyl radical as defined above and $R_h$ is an heterocyclyl radical as defined above, e.g., 1-tetrazolylethoxy, oxiranylmethoxy, and the like. For $R^3$, preferred heterocyclylalkoxy radicals are those radicals where $R_h$ is selected from the group consisting of oxiranyl or tetrazolyl. For $R^4$, preferred heterocyclylalkoxy radicals are those radicals where $R_h$ is pyrrolidinyl (optionally substituted by one or more substituents independently selected from the group consisting of hydroxy and carboxy).

"Heteroarylalkoxy" refers to a heterocyclylalkoxy radical as defined above wherein the heterocyclyl radical is partially or fully aromatic.

"Heterocyclylcarbonyl" refers to a radical of the formula —C(O)—$R_h$ where $R_h$ is a heterocyclyl radical as defined above, e.g., furan-2-ylcarbonyl, piperidin-4-ylcarbonyl, thien-2-ylcarbonyl, morpholin-4-ylcarbonyl, and the like. For $R^1$, preferred heterocyclylcarbonyl radicals are those radicals wherein $R_h$ is selected from the group consisting of furanyl, thienyl, piperidinyl, morpholinyl and pyridinyl (optionally substituted by one or more substitutents independently selected from the group consisting of hydroxy, halo and alkyl).

"Monoalkylamino" refers to a radical of the formula —N(H)—$R_a$ where $R_a$ is an alkyl radical as defined above, e.g., methylamino, ethylamino, n-propylamino, and the like.

"Monoalkylaminocarbonyl" refers to a radical of the formula —C(O)—N(H)—$R_a$ where $R_a$ is an alkyl radical as defined above, e.g., methylaminocarbonyl, ethylaminocarbonyl, n-propylaminocarbonyl, and the like.

"Mammal" includes humans and domesticated animals, such as cats, dogs, swine, cattle, sheep, goats, horses, rabbits, and the like.

"Nitro" refers to the —$NO_2$ radical.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7–9, 21–24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a human in need thereof, is sufficient to effect treatment, as defined below, for a disease-state characterized by thrombotic activity. The amount of a compound of the invention which constitutes a "therapeutically effective amount" will vary depending on the compound, the condition and its severity, and the age of the human to be treated, but can be determined routinely by one of ordinary skill in the art having regard to his own knowledge and to this disclosure.

"Treating" or "treatment" as used herein covers the treatment of a disease-state in a mammal, preferably a human, which disease-stated is characterized by thrombotic activity, and includes:

(i) preventing the condition from occurring in a human, in particular, when such human is predisposed to the condition but has not yet been diagnosed as having it;

(ii) inhibiting the condition, i.e., arresting its development; or (iii) relieving the condition, i.e., causing regression of the condition.

In the above definitions, the use of parentheses in a formula is used to conserve space. Accordingly, the use of parenthesis in a formula indicates that the group enclosed within the parentheses is attached directly to the atom preceding the parenthesis. For example, the term "(carboxy) (hydroxy)alkyl" is defined as a radical of the formula —R$_a$(OH)—C(O)OH. This formula can be drawn as follows:

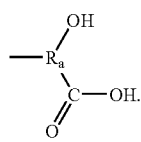

It will also be appreciated that certain compounds of the invention or pharmaceutically acceptable salts thereof, may exist in, and be isolated in, isomeric forms, including tautomeric forms, cis- or trans-isomers. In addition, certain compounds of the invention or pharmaceutically acceptable salts thereof may contain one or more asymmetric centers and may thus give rise to enantiomers, diastereomers, and other stereoisomeric forms that may be defined, in terms of absolute stereochemistry, such as (R)- or (S)-. The present invention is meant to include all such possible isomers, as well as their racemic and optically pure forms. Optically active (R)- and (S)-isomers may be prepared using chiral synthons or chiral reagents by methods known to those of ordinary skill in the art, or resolved using conventional techniques. When the compounds described herein contain olefinic double bonds or other centers of geometric asymmetry, and unless specified otherwise, it is intended that the compounds include both E and Z geometric isomers.

The nomenclature used herein is a modified form of the I.U.P.A.C. nomenclature system wherein the compounds of the invention are named herein as derivatives of the quinoline moiety.

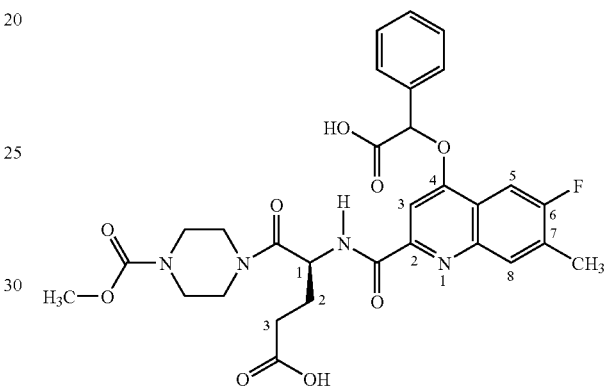

is named herein as 2-[1S-(4-(methoxycarbonyl)piperazin-1-yl)carbonyl-3-carboxypropyl]aminocarbonyl-6-fluoro-7-methyl-4-(1-phenyl-1-carboxy)methoxyquinoline. Unless otherwise indicated, compound names are intended to include any single stereoisomer, enantiomer, racemate or mixtures thereof.

Utility of the Compounds of the Invention

The compounds of the invention act as reversible, selective antagonists of the platelet ADP receptor, P2Y$_{AC}$. Accordingly, the compounds are useful in treating disease-states which are characterized as having thrombotic activity. In particular, the compounds are useful as inhibitors of platelet activation, aggregation and degranulation, anti-thrombotic agents or in the treatment or prophylaxis of unstable angina, coronary angioplasty (PTCA), myocardial infarction, perithrombolysis, primary arterial thrombotic I complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopenic purpura, hemolytic uremic syndrome, thrombotic complications of septicernia, adult respiratory distress syndrome, anti-phospholipid syndrome, heparin-induced thrombocytopaenia and pre-eclampsia/eclampsia, or venous thrombosis such as deep vein thrombosis, venoocclusive disease, hematological conditions such as myeloproliferative disease, including thrombocythemia; or in the prevention of mechanically-induced platelet activation in vivo, such as cardiopulmonary bypass (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, atheromatous plaque formation/progression, vascular stenosis/restenosis and asthma, in which platelet-derived factors are implicated in the disease process.

The compounds of formula (I) are also useful as standard or reference compounds, for example, as a quality standard or control, in tests or assays involving the inhibition of the platelet ADP receptor, $P2Y_{AC}$. Such compounds may be provided in a commercial kit, for example, for use in pharmaceutical research involving the platelet ADP receptor, $P2Y_{AC}$. For example, a compound of formula (I) could be used as a reference in an assay to compare its known activity to a compound with an unknown activity. This would ensure that the experimenter that the assay was being performed properly and provide a basis for comparison, especially if the test compound was a derivative of the reference compound. When developing new assays or protocols, compounds of formula (I) could be used to test their effectiveness.

Testing of the Compounds of the Invention

The ability of the compounds to inhibit the platelet adenosine diphosphate receptor known as the $P2Y_{AC}$ receptor, and its biological effects may be tested in a variety of in vitro, ex vivo and in vivo assays. For example, the ability of the compounds to bind to the $P2Y_{AC}$ receptor may be measured by methods similar to those described in Gachet, C. et al., *Br. J. Haemotol.* (1995), Vol. 91, pp. 434–444 and Mills, D. C. B., *Thromb. Haemost.* (1996), Vol. 76, No. 6, pp. 835–856, and by the method described below in Example 4. The ability of the compounds to inhibit ADP-induced aggregation of platelets may be measured by methods similar to those described in R. G. Humphries, *Br. J. Pharm.* (1995), Vol. 115, pp. 1110–1116 and *Methods in Enzymology*, Vol. 169, p. 3 and by the method described below in Example 5. The ability of the compounds to inhibit thrombus formation in vivo or ex vivo may be measured by methods similar to those described in J. M. Herbert, *Cardiovasc. Drug Reviews* (1993), Vol. 11, No. 2, pp. 180–198 or J. D. Folts, *Circulation* (1976), Vol. 54, No. 3, p. 365, or by the methods described below in Example 6. The results of these assays clearly demonstrate that the compounds of the invention are functional antagonists of the platelet adenosine diphosphate receptor and are thereful useful in inhibiting platelet aggregation and thrombus formation.

Administration of the Compounds of the Invention

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state characterized by thrombotic activity in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

PREFERRED EMBODIMENTS

Of the compounds of the invention as set forth above in the Summary of the Invention, several groups of compounds are particularly preferred.

Of the compounds of formula (I) as set forth above in the Summary of the Invention, a preferred group of compounds is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aryl optionally substituted by one or more substituents selected from the group consisting of alkyl, halo, haloalkyl, cyano, nitro, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, and $-R^8-N(R^7)C(O)OR^9$;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
$R^5$ is hydrogen;
$R^6$ is hydrogen or alkyl;
each $R^7$ is hydrogen, alkyl, aryl, aralkyl, or haloalkyl;
each $R^8$ is a bond or a straight or branched alkylene chain; and
$R^9$ is hydrogen, alkyl, aralkyl or haloalkyl.

Of this preferred group of compounds, a preferred subgroup of compounds is that subgroup of compounds wherein:
m is 1;
n is 1 or 2;
$R^1$ is hydrogen or alkoxycarbonyl;
$R^2$ is hydrogen, carboxyalkyl, alkoxycarbonylalkyl or aralkoxycarbonylalkyl;
$R^3$ is aryl optionally substituted by one or more substituents selected from the group consisting of carboxy or alkoxycarbonyl;
each $R^4$ is is independently selected from the group consisting of hydrogen, alkyl, halo, or haloalkyl;
$R^5$ is hydrogen; and
$R^6$ is hydrogen.

Of this preferred subgroup of compounds, a preferred compound is 2-[1S-(4-(ethoxycarbonyl)piperazin-1-yl)carbonyl-3-carboxypropyl]aminocarbonyl-4-(3-carboxy)phenylquinoline in trifluoroacetic acid.

Another preferred group of compounds of formula (I) is that group of compounds wherein:
m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aryloxy optionally substituted by one or more substituents selected from the group consisting of alkyl, halo, haloalkyl, cyano, nitro, tetrazolyl, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
$R^5$ is selected from the group consisting of hydrogen, alkyl, hydroxyalkyl, aralkyl, carboxy, alkoxycarbonyl, aralkoxycarbonyl, carboxyalkyl, and alkoxycarbonylalkyl;
$R^6$ is hydrogen, alkyl, carboxyalkyl, or alkoxycarbonylalkyl;
each $R^7$ is hydrogen, alkyl, aryl, aralkyl, or haloalkyl;
each $R^8$ is a bond or a straight or branched alkylene chain; and
$R^9$ is hydrogen, alkyl, aralkyl or haloalkyl.

Of this preferred group of compounds, a preferred subgroup of compounds is that subgroup of compounds wherein:
m is 1;
n is 1 or 2;
$R^1$ is hydrogen or alkoxycarbonyl;
$R^2$ is hydrogen, carboxyalkyl, alkoxycarbonylalkyl or aralkoxycarbonylalkyl;
$R^3$ is aryloxy optionally substituted by one or more substituents selected from the group consisting of alkyl, tetrazolyl, $-R^8-C(O)OR^7$, $-R^8-N(R^7)_2$, $-R^8-N(R^7)-S(O)_2-R^7$, and $-R^8-C[N(R^7)_2]-C(O)OR^7$;
each $R^4$ is is independently selected from the group consisting of hydrogen, alkyl, halo, or haloalkyl;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

Of this preferred subgroup of compounds, preferred compounds are selected from the group consisting of the following:

2-[1S-(4-(ethoxycarbonyl)piperazin-1-yl)carbonyl-3-carboxypropyl]aminocarbonyl-4-(3-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(2-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(2-amino-5-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(4-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(3-carboxymethyl)phenoxyquinoline in trifluoroacetic acid;

2-[1S-(4-(ethoxycarbonyl)piperazin-1-yl)carbonyl-3-carboxypropyl]aminocarbonyl-4-(3-(1-amino-1-carboxy)methyl)phenoxyquinoline in trifluoroacetic acid;

2-[1S-(4-(ethoxycarbonyl)piperazin-1-yl)carbonyl-3-carboxypropyl]aminocarbonyl-4-(3-(2-amino-2-carboxy)ethyl)phenoxyquinoline in trifluoroacetic acid;

2-[1S-(4-(ethoxycarbonyl)piperazin-1-yl)carbonyl-3-carboxypropyl]aminocarbonyl-4-(2-methyl-5-carboxy)phenoxyquinoline in trifluoroacetic acid;

2-[1S-(4-(ethoxycarbonyl)piperazin-1-yl)carbonyl-3-carboxypropyl]aminocarbonyl-4-(5-carboxy-2-diethylaminomethyl)phenoxyquinoline in trifluoroacetic acid;

2-[1S-(4-(ethoxycarbonyl)piperazin-1-yl)carbonyl-3-carboxypropyl]aminocarbonyl-4-(3-tetrazol-5-yl)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(3-trifluoromethylsulfonylamino)phenoxyquinoline in trifluoroacetic acid; and 2-[1S-(4-(ethoxycarbonyl)piperazin-1-yl)carbonyl-3-carboxypropyl]aminocarbonyl-7-methyl-4-(3-carboxy)phenoxyquinoline in trifluoroacetic acid.

Another preferred group of compounds of formula (I) is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aralkyl wherein the alkyl radical in the aralkyl substituent is optionally substituted by one or more substituents selected from the group consisting of halo, cyano, nitro, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, and $-R^9-N(R^7)C(O)OR^9$, and wherein the aryl radical in the aralkyl substituent is independently optionally substituted by one or more substituents selected from the group consisting of alkyl, halo, haloalkyl, cyano, nitro, tetrazolyl, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
$R^5$ is selected from the group consisting of hydrogen, alkyl, hydroxyalkyl, aralkyl, carboxy, alkoxycarbonyl, aralkoxycarbonyl, carboxyalkyl, and alkoxycarbonylalkyl;
$R^6$ is hydrogen, alkyl, carboxyalkyl, or alkoxycarbonylalkyl;
each $R^7$ is hydrogen, alkyl, aryl, aralkyl, or haloalkyl;
each $R^8$ is a bond or a straight or branched alkylene chain; and
$R^9$ is hydrogen, alkyl, aralkyl or haloalkyl.

Another preferred group of compounds of formula (I) is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aralkoxy wherein the alkyl radical in the aralkyl substituent is not optionally substituted and wherein the aryl radical in the aralkoxy substituent is optionally substituted by one or more substituents selected from the group consisting of alkyl, halo, haloalkyl, cyano, nitro, tetrazolyl, $-R^8-OR^7$, $-R^8-C(O)OR^7$, $-R^8-C(O)N(R^7)_2$, $-R^8-C(O)R^7$, $-R^8-N(R^7)_2$, $-R^8-N(R^7)C(O)R^7$, $-R^8-N(R^7)C(O)OR^9$, $-R^8-N(R^7)-S(O)_2-R^7$, and $-R^8-C[N(R^7)_2]-C(O)OR^7$;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
$R^5$ is selected from the group consisting of hydrogen, alkyl, hydroxyalkyl, aralkyl, carboxy, alkoxycarbonyl, aralkoxycarbonyl, carboxyalkyl, and alkoxycarbonylalkyl;
$R^6$ is hydrogen, alkyl, carboxyalkyl, or alkoxycarbonylalkyl;
each $R^7$ is hydrogen, alkyl, aryl, aralkyl, or haloalkyl;
each $R^8$ is a bond or a straight or branched alkylene chain; and
$R^9$ is hydrogen, alkyl, aralkyl or haloalkyl.

Of this preferred group of compounds, a preferred subgroup of compounds is that subgroup of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aralkoxy wherein the aryl radical in the aralkoxy substituent is optionally substituted by one or more substituents selected from the group consisting of alkyl, halo, haloalkyl, $-R^8-OR^7$, $-R^8-C(O)OR^7$, $-R^8-C(O)N(R^7)_2$, and $-R^8-N(R^7)_2$;
each $R^4$ is independently selected from the group consisting of hydrogen, alkyl, alkoxy, halo, or haloalkyl;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

Of this preferred subgroup of compounds, preferred compounds are selected from the group consisting of the following:

2-[(4-(ethoxycarbonyl)piperazin-1-yl)carbonylmethyl]aminocarbonyl-4-benzyloxyquinoline;

2-[1S-(4-(ethoxycarbonyl)piperazin-1-yl)carbonyl-3-benzyloxycarbonylpropyl]aminocarbonyl-4-benzyloxyquinoline;

2-[1S-(4-(ethoxycarbonyl)piperazin-1-yl)carbonyl-3-carboxypropyl]aminocarbonyl-4-benzyloxyquinoline;

2-[1-(4-(ethoxycarbonyl)piperazin-1-yl)carbonyl-3-benzyloxycarbonylpropyl]aminocarbonyl-4-benzyloxy-8-methoxyquinoline;

2-[1S-(4-(ethoxycarbonyl)piperazin-1-yl)carbonyl-3-carboxypropyl]aminocarbonyl-4-benzyloxy-8-methoxyquinoline;

2-[(4-(ethoxycarbonyl)piperazin-1-yl)carbonylmethyl]aminocarbonyl-4-(4-methoxycarbonyl)benzyloxyquinoline;

2-[(4-(ethoxycarbonyl)piperazin-1-yl)carbonylmethyl]aminocarbonyl-4-(4-carboxy)benzyloxyquinoline;

2-[(4-(ethoxycarbonyl)piperazin-1-yl)carbonylmethyl]aminocarbonyl-4-(3-methoxycarbonyl)benzyloxyquinoline;

2-[(4-(ethoxycarbonyl)piperazin-1-yl)carbonylmethyl]aminocarbonyl-4-(3-carboxy)benzyloxyquinoline;

2-[1S-(4-(3-methylphenyl)piperazin-1-yl)carbonyl-3-(1,1-dimethylethoxycarbonyl)propyl]aminocarbonyl-4-benzyloxyquinoline; and 2-[1S-(4-(3-methylphenyl)piperazin-1-yl)carbonyl-3-carboxypropyl]aminocarbonyl-4-benzyloxyquinoline.

Another preferred group of compounds of formula (I) is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aralkoxy wherein the alkyl radical in the aralkoxy substituent is substituted by one or more substituents selected from the group consisting of halo, cyano, nitro, $—R^8—OR^7$, $—R^8—C(O)OR^7$, $—R^8—C(O)N(R^7)_2$, $—R^8—C(O)R^7$, $—R—N(R^7)_2$, $—R^8—N(R^7)C(O)R^7$, and $—R^9—N(R^7)C(O)OR^9$), and wherein the aryl radical in the aralkoxy substituent is optionally substituted by one or more substituents selected from the group consisting of alkyl, halo, haloalkyl, cyano, nitro, tetrazolyl, $—R^8—OR^7$, $—R^8—C(O)OR^7$, $—R^8—C(O)N(R^7)_2$, $—R^8—C(O)R^7$, $—R^8—N(R^7)_2$, $—R^8—N(R^7)C(O)R^7$, $—R^8—N(R^7)C(O)OR^9$, $—R^8—N(R^7)—S(O)_2—R^7$, and $—R^8—C[N(R^7)_2]—C(O)OR^7$;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
$R^5$ is selected from the group consisting of hydrogen, alkyl, hydroxyalkyl, aralkyl, carboxy, alkoxycarbonyl, aralkoxycarbonyl, carboxyalkyl, and alkoxycarbonylalkyl;
$R^6$ is hydrogen, alkyl, carboxyalkyl, or alkoxycarbonylalkyl;
each $R^7$ is hydrogen, alkyl, aryl, aralkyl, or haloalkyl;
each $R^8$ is a bond or a straight or branched alkylene chain; and
$R^9$ is hydrogen, alkyl, aralkyl or haloalkyl.

Of this preferred group of compounds, a preferred subgroup of compounds is that subgroup of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is aralkoxy wherein the alkyl radical in the aralkoxy substituent is substituted by $—R^8—C(O)OR^7$, and wherein the aryl radical in the aralkoxy substituent is optionally substituted by one or more substituents selected from the group consisting of halo and $—R^8—OR^7$;
each $R^4$ is independently selected from the group consisting of hydrogen, alkyl, alkoxy, halo, haloalkyl, amino, monoalkylamino, or dialkylamino;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

Of this preferred subgroup of compounds, preferred compounds are selected from the group consisting of the following:

2-[1S-(4-(ethoxycarbonyl)piperazin-1-yl)carbonyl-3-(1,1-dimethylethoxycarbonyl)propyl]aminocarbonyl-4-(1-phenyl-1-methoxycarbonyl)methoxyquinoline;

2-[1S-(4-(ethoxycarbonyl)piperazin-1-yl)carbonyl-3-carboxypropyl]aminocarbonyl-4-(1-phenyl-1-methoxycarbonyl)methoxyquinoline;

2-[1S-(4-(ethoxycarbonyl)piperazin-1-yl)carbonyl-3-carboxypropyl]aminocarbonyl-4-(1-phenyl-1-carboxy)methoxyquinoline;

2-[1S-(4-(ethoxycarbonyl)piperazin-1-yl)carbonyl-3-carboxypropyl]aminocarbonyl-7-methyl-4-(1-phenyl-1-carboxy)methoxyquinoline;

2-[1S-(4-(ethoxycarbonyl)piperazin-1-yl)carbonyl-3-carboxypropyl]aminocarbonyl-6-fluoro-7-methyl-4-(1-phenyl-1-carboxy)methoxyquinoline;

2-[1S-(4-(ethoxycarbonyl)piperazin-1-yl)carbonyl-3-carboxypropyl]aminocarbonyl-7-chloro-4-(1-carboxy-1-phenyl)methoxyquinoline in trifluoroacetic acid;

2-[1S-(4-(ethoxycarbonyl)piperazin-1-yl)carbonyl-3-carboxypropyl]aminocarbonyl-6-fluoro-7-methyl-4-(1-naphth-1-yl-1-carboxy)methoxyquinoline;

2-[1S-(4-(ethoxycarbonyl)piperazin-1-yl)carbonyl-3-carboxypropyl]aminocarbonyl-6-chloro-8-fluoro-4-(1-methoxycarbonyl-1-phenyl)methoxyquinoline in acetic acid;

2-[1S-(4-(ethoxycarbonyl)piperazin-1-yl)carbonyl-3-carboxypropyl]aminocarbonyl-6-chloro-8-fluoro-4-(1-carboxy-1-phenyl)methoxyquinoline in acetic acid;

2-[1S-(4-(ethoxycarbonyl)piperazin-1-yl)carbonyl-3-carboxypropyl]aminocarbonyl-7-methyl-6-fluoro-4-(1-carboxy-1-(2-fluoro)phenyl)methoxyquinoline in trifluoroacetic acid;

2-[1S-(4-(ethoxycarbonyl)piperazin-1-yl)carbonyl-3-carboxypropyl]aminocarbonyl-7-methyl-4-(1-ethoxycarbonyl-1-phenyl)methoxyquinoline in trifluoroacetic acid;

2-[(4-(ethoxycarbonyl)piperazin-1-yl)carbonylmethyl]aminocarbonyl-6-fluoro-7-methyl-4-(1-phenyl-1-carboxy)methoxyquinoline;

2-[1S-(4-(ethoxycarbonyl)piperazin-1-yl)carbonyl-3-carboxypropyl]aminocarbonyl-7-methyl-6-fluoro-4-(1-carboxy-1-(4-chloro)phenyl)methoxyquinoline in trifluoroacetic acid;

2-[1S-(4-(ethoxycarbonyl)piperazin-1-yl)carbonyl-3-carboxypropyl]aminocarbonyl-7-methyl-6-fluoro-4-(1-carboxy-1-(3-methoxy)phenyl)methoxyquinoline in trifluoroacetic acid;

2-[1S-(4-(ethoxycarbonyl)piperazin-1-yl)carbonyl-3-carboxypropyl]aminocarbonyl-6,8-difluoro-4-(1-carboxy-1-phenyl)methoxyquinoline in trifluoroacetic acid;

2-[1S-(4-(ethoxycarbonyl)piperazin-1-yl)carbonyl-3-carboxypropyl]aminocarbonyl-6-dimethylamino-4-(1-phenyl-1-carboxy)methoxyquinoline;

2-[1S-(4-(ethoxycarbonyl)piperazin-1-yl)carbonyl-3-carboxypropyl]aminocarbonyl-7-chloro-6-methyl-4-(1-phenyl-1-carboxy)methoxyquinoline in trifluoroacetic acid;

2-[1S-(4-(ethoxycarbonyl)piperazin-1-yl)carbonyl-3-carboxypropyl]aminocarbonyl-7-methyl-6-chloro-4-(1-phenyl-1-carboxy)methoxyquinoline in trifluoroacetic acid;

2-[1S-(4-(1,1-dimethylethoxycarbonyl)piperazin-1-yl)carbonyl-3-methoxycarbonylpropyl]aminocarbonyl-6-fluoro-7-methyl-4-(1-phenyl-1-carboxy)methoxyquinoline;

2-[1S-(4-(1,1-dimethylethoxycarbonyl)piperazin-1-yl)carbonyl-3-carboxypropyl]aminocarbonyl-6-fluoro-7-methyl-4-(1-phenyl-1-carboxy)methoxyquinoline;

2-[1S-(4-(methoxycarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(1,1-dimethylethylaminocarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(furan-2-ylcarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(3-methylphenyl)piperazin-1-yl)carbonyl-3-(1,1-dimethylethoxycarbonyl)propyl]aminocarbonyl-6-fluoro-7-methyl-4-(1-phenyl-1-carboxy)methoxyquinoline;

2-[1S-(4-(3-methylphenyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(phenyl)piperazin-1-yl)carbonyl-3-(1,1-dimethylethoxycarbonyl)propyl]aminocarbonyl-6-fluoro-7-methyl-4-(1-phenyl-1-carboxy)methoxyquinoline; and 2-[1S-(4-(phenyl)piperazin-1-yl)carbonyl-3-carboxypropyl]aminocarbonyl-6-fluoro-7-methyl-4-(1-phenyl-1-carboxy)methoxyquinoline in trifluoroacetic acid.

Of the compounds of formula (II) as set forth above in the Summary of the Invention, a preferred group of compounds is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is heteroaryl optionally substituted by one or more substituents selected from the group consisting of alkyl, halo, haloalkyl, $-R^8-OR^7$, $-R^8-C(O)OR^7$, $-R^8-C(O)N(R^7)_2$, and $-R^8-N(R^7)_2$;
each $R^4$ is independently selected from the group consisting of hydrogen, alkyl, alkoxy, halo, haloalkyl, amino, monoalkylamino, or dialkylamino;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

Of this preferred group of compounds, a preferred compound is 2-[1S-(4-(ethoxycarbonyl)piperazin-1-yl)carbonyl-3-carboxypropyl]aminocarbonyl-4-(1, 2,3,4-tetrahydroisoquinolin-2-yl)quinoline in trifluoroacetic acid.

Another preferred group of compounds of formula (II) is that group of compounds wherein:

m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is heteroarylalkoxy, wherein the alkoxy radical in the heteroarylalkoxy substituent is optionally substituted by one or more substituents selected from the group consisting of halo and $-R^8-C(O)OR^7$, and wherein the heteroaryl radical in the heteroarylalkoxy substituent is independently optionally substituted by one or more substituents selected from the group consisting of alkyl, halo, haloalkyl, $-R^1-OR^7$, $-R^8-C(O)OR^7$, $-R^8-C(O)N(R^7)_2$, and $-R^8-N(R^7)_2$;
each $R^4$ is independently selected from the group consisting of hydrogen, alkyl, alkoxy, halo, haloalkyl, amino, monoalkylamino, or dialkylamino;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

Of this preferred group of compounds, preferred compounds are selected from the group consisting of the following:

2-[1S-(4-(ethoxycarbonyl)piperazin-1-yl)carbonyl-3-carboxypropyl]aminocarbonyl-4-(5-methylisoxaxol-3-yl)methoxyquinoline in trifluoroacetic acid;

2-[1S-(4-(ethoxycarbonyl)piperazin-1-yl)carbonyl-3-carboxypropyl]aminocarbonyl-4-(2-methylthiazol-4-yl)methoxyquinoline in trifluoroacetic acid;

2-[1S-(4-(ethoxycarbonyl)piperazin-1-yl)carbonyl-3-methoxycarbonylpropyl]aminocarbonyl-4-(1-phenyl-1-ethoxycarbonyl-1-chloro)methoxyquinoline;

2-[1-(4-(ethoxycarbonyl)piperazin-1-yl)carbonyl-3-carboxypropyl]aminocarbonyl-7-methyl-6-fluoro-4-(1-carboxy-1-thien-3-yl)methoxyquinoline in trifluoroacetic acid;

2-[1S-(4-(ethoxycarbonyl)piperazin-1-yl)carbonyl-3-carboxypropyl]aminocarbonyl-6-chloro-7-methyl-4-(5-methylisoxazol-3-yl)methoxyquinoline; and 2-[1-(4-(ethoxycarbonyl)piperazin-1-yl)carbonyl-3-carboxypropyl]aminocarbonyl-6-chloro-7-methyl-4-(2-methylthiazol-4-yl)methoxyquinoline in trifluoroacetic acid.

Preparation of the Compounds of the Invention

The compounds of the invention are prepared according to the methods described below in the following Reaction Schemes. It is understood that those compounds of the invention which are not specifically prepared in the following Reaction Schemes may be prepared by similar synthetic processes with the appropriately substituted starting materials and reagents. It is also understood that during the preparation of the compounds of the invention, as described below, additional reactive groups (for example, hydroxy, amino or carboxy groups) on the intermediate compounds utilized in the preparation may be protected as needed by the appropriate protecting group by treating the intermediate compound prior to the desired reaction with the appropriate protecting group precursor by methods known to those of ordinary skill in the art. The protecting groups may then be removed as desired by methods known to those of ordinary skill in the art, for example, by acidic or basic hydrolysis. Such protecting groups and methods are described in detail in Greene, T. W. and Wuts, P. G. M., *Protective Groups in Organic Synthesis*, 2nd Edition, 1991, John Wiley & Sons. Preferred nitrogen-protecting groups are "Boc" (t-butoxycarbonyl) and "CBZ" (benzyloxycarbonyl).

It will also be appreciated by those skilled in the art, although such protected derivatives of compounds of the invention as described above in the Summary of the Invention, may not possess pharmacological activity as such, they may be administered to a mammal having a disease-state characterized by thrombotic activity and thereafter metabolized in the body to form compounds of the invention which are pharmacologically active. Such derivatives may therefore be described as "prodrugs". All prodrugs of compounds of the invention are included within the scope of the invention.

It is understood that in the following description, combinations of substituents and/or variables of the depicted formulae are permissible only if such conbinations result in stable compounds which can be isolated by methods known to those of ordinary skill in the art. Transient compounds are indicated by brackets.

For purposes of convenience, the preparation of compounds of formula (I) (where $R^3$ is aryl, aralkyl, aryloxy or aralkoxy) are only described below. However, one of ordinary skill in the art would understand that in order to prepare the corresponding compounds of formula (II), all that one would need to do is replace the pertinent intermediates (such as compounds of formula (J)) with the appropriate compound (such as compounds of formula (J) where $R^{3a}$ is heteroarylalkyl) and to adjust the experimental parameters accordingly.

A. Preparation of Compounds of formula (D)

Compounds of formula (D) are intermediates used in the preparation of the compounds of the invention. They may be prepared as described below in Reaction Scheme 1 wherein m, $R^1$, $R^2$, $R^5$, and $R^6$ are as described above in the Summary of the Invention; PG is a nitrogen-protecting group; and $R^{1a}$ is hydrogen (or a nitrogen protecting group if $R^1$ is hydrogen):

treated under standard hydrolysis conditions to form a compound of formula (D), which is isolated form the reaction mixture by filtration.

Alternatively, compounds of formula (A) where $R^1$ is hydrogen and $R^{1a}$ is a nitrogen protecting group can be treated with the appropriately subsituted acid halide, carbamoyl halide or isocyanate to yield the corresponding appropriately substituted compounds of formula (A), which can then be treated to standard deprotecting procedures to remove the $R^{1a}$ nitrogen protecting group prior to being reacted with the compound of formula (B) to form compounds of formula (C) and (D) wherein $R^1$ is as described above in the Summary of the Invention.

B. Preparation of Compounds of formula (H)

Compounds of formula (H) are intermediates in the preparation of compounds of formula (I) and are prepared as described below in Reaction Scheme 2a wherein n is as described as above in the Summary of the Invention; $R^4$ is as described above in the Summary of the Invention; and $R^{10}$ is alkyl or aralkyl:

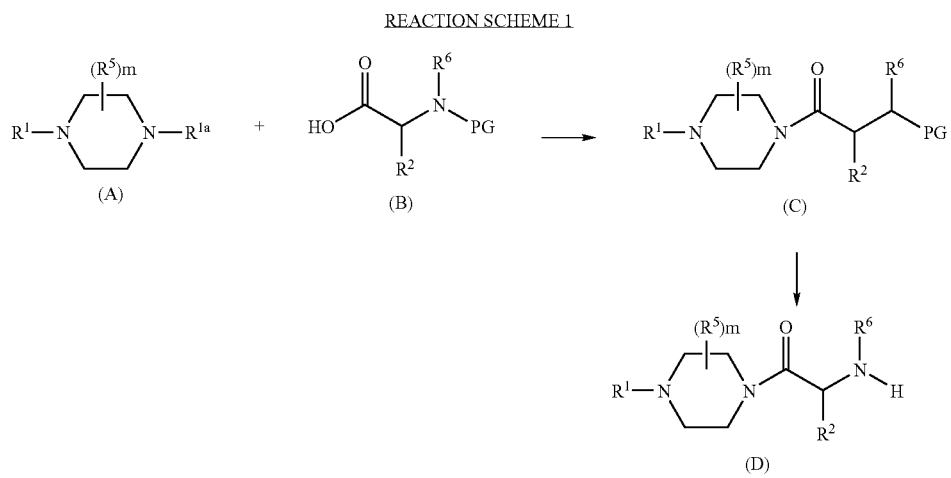

Compounds of formulae (A) and (B) are commercially available, for example, from Aldrich, or may be prepared according to methods known to those of ordinary skill in the art, or by methods as described herein.

In general, compounds of formula (D) are prepared by first treating a compound of formula (B) in an aprotic solvent mixture, such as tetrahydrofuran (THF) and methylene chloride, with a slightly excess molar amount of a peptide coupling reaction additive, such as 1-hydroxybenzotriazole (HOBT) and a slightly excess molar amount of coupling agent for amide formation, such as 1-(3-dimethylaminopropyl)-3-ethylcarbodiimide (EDCI) at ambient temperature. To this mixture is added a slightly excess molar amount of a compound of formula (A) where $R^{1a}$ is hydrogen and the resulting reaction mixture is allowed to stir overnight at ambient temperature. The compound of formula (C) is isolated from the reaction mixture by standard isolation techniques, such as evaporation and extraction.

Depending on what PG is, the compound of formla (C) is then reduced under standard hydrogenation conditions, such as treatment with pladium over carbon under hydrogen or

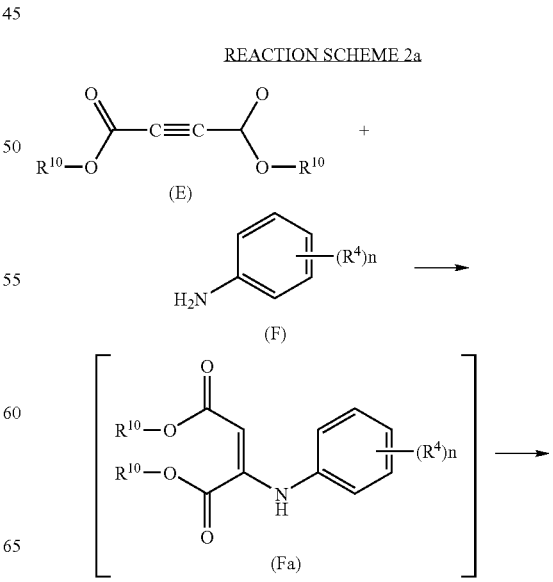

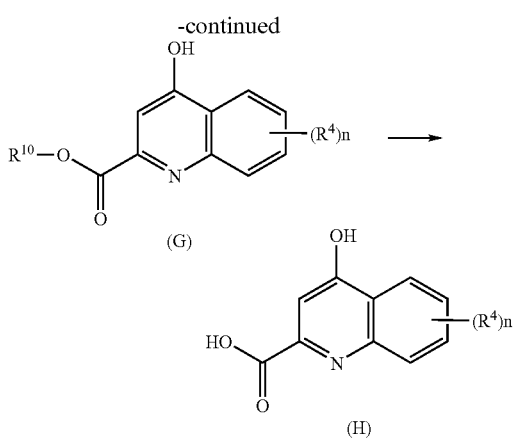

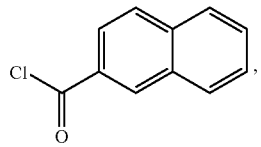

Compounds of formulae (E), and (F) are commercially available, for example, from Aldrich, or may be prepared according to methods known to those of ordinary skill in the art. Compounds of formula (G) and formula (H) may alternatively be prepared by methods disclosed in Great Britain Patent No. 1,334,705.

In general, compounds of formula (H) are prepared by first treating a compound of formula (F) in a protic solvent, such as methanol, with an equimolar amount of a compound of formula (E) with stirring at ambient temperature for about 30 minutes to about an hour, preferably for about 30 minutes. The solvent is removed by evaporation to form a residue.

To an aprotic polar solvent, such as diphenyl ether, heated to between about 200° C. and about 250° C., preferably to about 250° C. is then added the residue and the temperature of the reaction mixture is maintained at the high temperature for about 30 minutes to an hour, preferably for about 30 minutes, at which point the reaction mixture is allowed to cool to ambient temperature. The resulting precipitate is collected and washed with a aprotic polar solvent, such as ether, which is previously heated to below boiling temperature, to give compounds of formula (G). Further purification, for example, by dissolving the mixture in a protic solvent at boiling temperature, such as methanol, and then allowing the mixture to cool to ambient temperature for a period of about 1 to about 2 days, preferably for about 2 days, yields a compound of formula (H), which is isolated from the reaction mixture by standard techniques.

Alternatively, compounds of formula (D) as prepared above in Reaction Scheme 1 can be reacted with compounds of the following structure:

which are commercially avaible or prepared by methods known to one of ordinary skill in the art, under standard acylation conditions to form additional compounds of the invention.

A preferred method of making intermediates used in the preparation of the compounds of the invention which avoids the formation of undesired regiosiomers with respect to the substitution on the quinoline ring is illustrated below in Reaction Scheme 2b wherein $R^{4a}$ is alkyl, alkoxy, aralkoxy, carboxy, alkoxycarbonyl, aminocarbonyl, alkylcarbonylamino, di(alkylcarbonyl)amino, carboxyalkoxy, alkoxycarbonylalkoxy or heterocyclylalkoxy; X is iodo, chloro or bromo; and $R^{10}$ is alkyl or aralkyl:

REACTION SHCEME 3

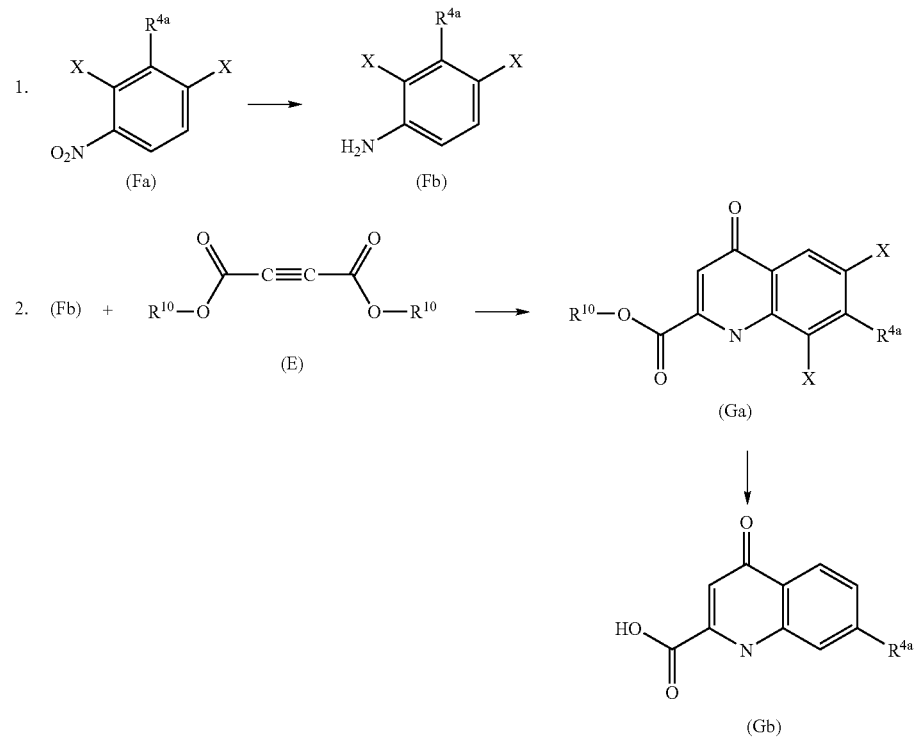

Compounds of formula (Fa) and formula (E) are commercially available, or can prepared according to methods known to those of ordinary skill in the art.

In general, compounds of formula (Gb) are prepared by first treating a compound of formula (Fa) with a reducing agent, such as tin (II) chloride dihydrate, under standard chemical reduction conditions, such as in a protic solvent, to form the compound of formula (Fb), which is isolated from the reaction mixture by standard isolation techniques.

The compound of formula (Fb) in a protic solvent, such as methanol, is then treated with a slightly excess molar amount of a compound of formula (E) at reflux temperatures for about 2 to about 4 hours, preferably for about 4 hours. The reaction mixture is then concentrated. An organic solvent is heated to a non-boiling point temperature of between about 240° C. and about 260° C., and the concentrate is then added to the solvent. The temperature of the mixture is maintained at the non-boiling point temperature for about 10 to 20 minutes, preferably for about 20 minutes. The reaction mixture is then cooled slowly to ambient temperature and diluted with an organic solvent. The compound of formula (Ga) is isolated from the reaction mixture by standard isolation techniques, such as filtration.

The compound of formula (Ga) is treated with a hydrolyzing agent under standard hydrolysis conditions and then treated under standard reducing conditions, such as hydrogen gas and palladium over carbon, to form a compound of formula (Gb).

Compounds of formula (Gb) may then be used instead of compounds of formula (H) in subsequent Reaction Schemes to prepare compounds of the invention.

C. Preparation of Compounds of Formula (Ia)

Compounds of formula (Ia) are compound of the invention and are prepared as described below in Reaction Scheme 3 wherein m, n, $R^1$, $R^2$, $R^4$, $R^5$, and $R^6$ are as defined above in the Summary of the Invention, $R^{3a}$ is aryl or aralkyl, and X is halo:

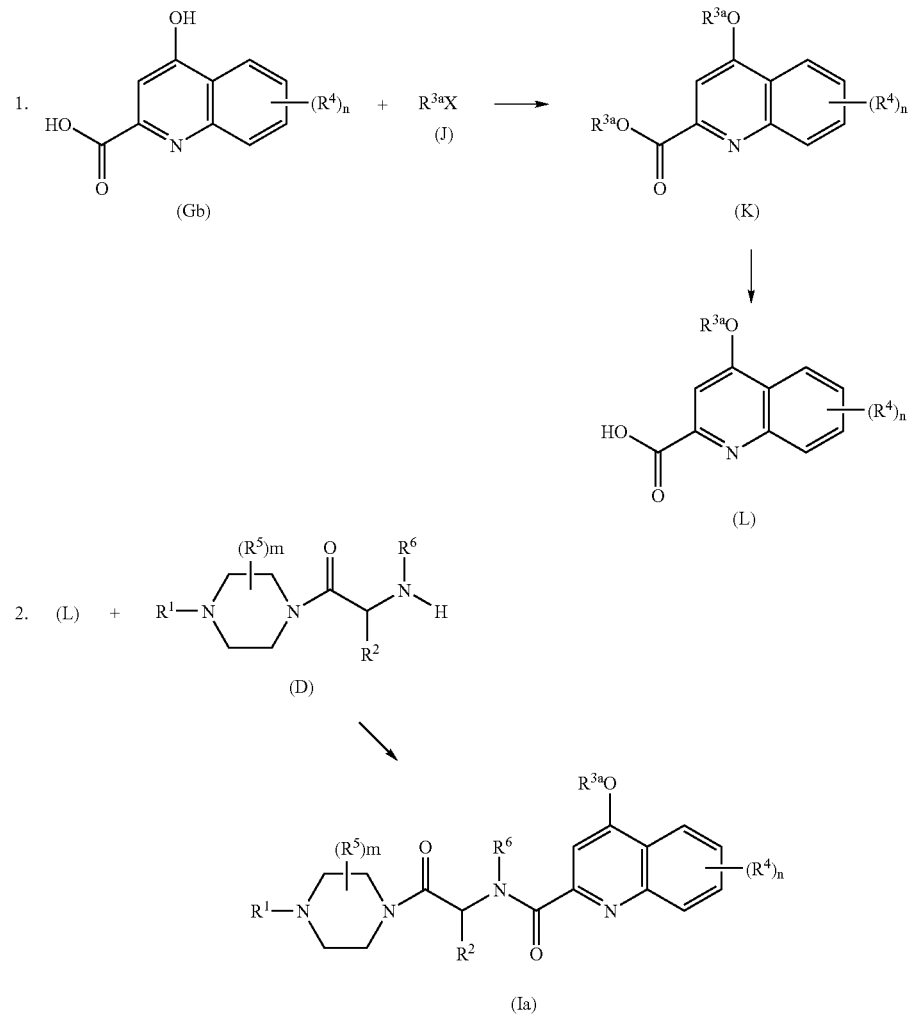

Compounds of formulae (D) and (H) are prepared by methods disclosed herein. Compounds of formula (J) are commercially available, for example, from Aldrich Co., or can be prepared according to methods known to one of ordinary skill in the art.

In general, compounds of formula (Ia) are prepared by first treating a compound of formula (H) under standard Williamson synthesis conditions, such as in the presence of a base in an aprotic solvent, for example, cesium carbonate in N,N-dimethylformamide ("DMF"), with an equimolar amount of a compound of formula (J) at temperatures between about ambient temperature and about 100° C. The reaction mixture is stirred from about 2 hours to about 10 hours, preferably for about 10 hours, to yield the compound of formula (K), which is then treated under standard hydrolysis conditions to yield the compound of formula (L).

The compound of formula (L) in an aprotic solvent mixture, for example, methylene chloride and DMF or methylene chloride and triethylamine, is then treated with a slightly excess molar amount of a peptide coupling reaction additive, such as 1-hydroxybenzotriazole ("HOBT") and a slightly excess molar amount a coupling agent for amide formation, such as 1-(3-dimethylaminopropyl)-3-ethylcarbodiimide ("EDCI") at ambient temperature. An equimolar amount of a compound of formula (D) in an aprotic solvent, such as methylene chloride, is then added to the reaction mixture. The reaction mixture is stirred at ambient temperature for about 4 to about 12 hours, preferably for about 12 hours. The compound of formula (Ia) is then isolated from the reaction mixture by standard isolation techniques, such as evaporation of the solvents, extraction and concentration.

If desired, compounds of formula (Ia) may be deprotected to yield the corresponding free acid or free amine derivatives. Furthermore, compounds of formula (Ia) wherein $R^1$ is a nitrogen-protecting group, such as an alkyl carbonyl, can be hydrolyzed under standard acid hydrolysis conditions to yield the corresponding compound of formula (Ia) wherein $R^1$ is hydrogen, which can then be treated with the appropriately substituted acid halide, carbamoyl halide or isocyanate to yield the appropriately substituted $R^1$ compound of formula (Ia).

D. Preparation of Compounds of Formula (Ib)

Compounds of formula (Ib) are compounds of the invention and are prepared as described below in Reaction Scheme 4 wherein n, $R^1$, $R^2$, $R^4$, $R^5$ and $R^6$ are as described above in the Summary of the Invention, $R^{3a}$ is aryl or aralkyl and X is halo:

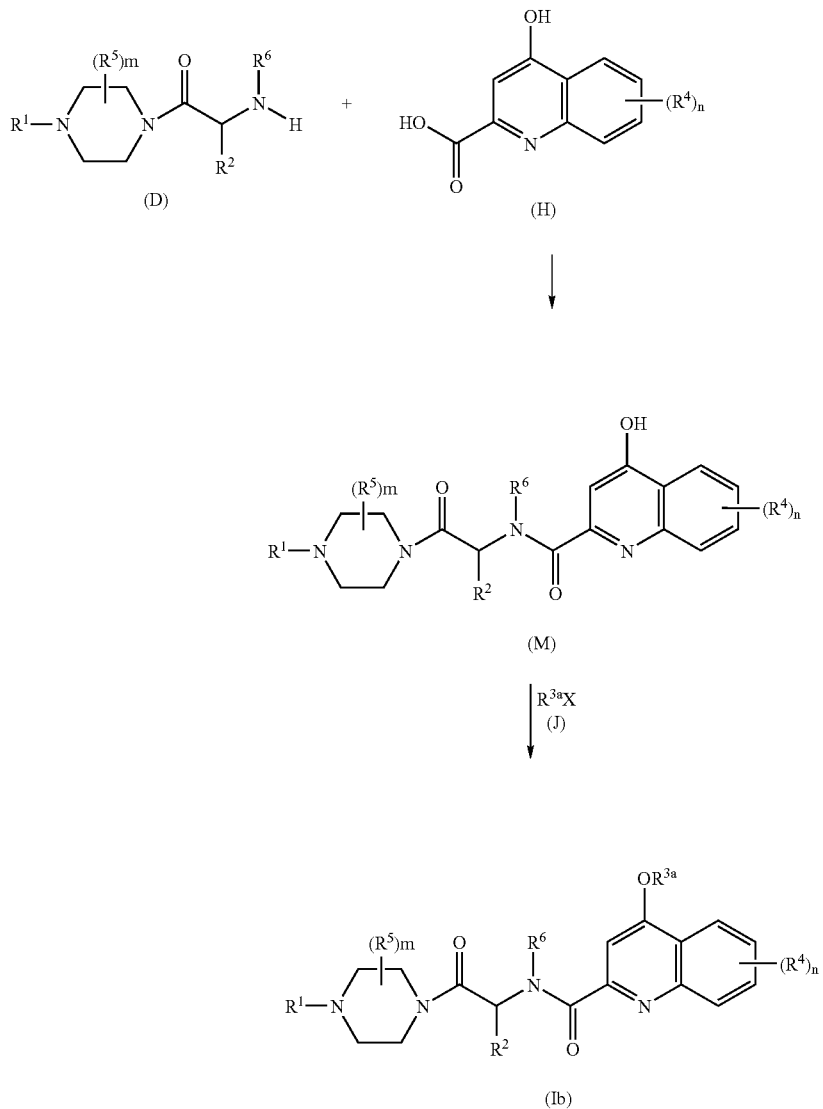

Compounds of formula (D) are prepared as described herein or may be prepared by methods known to one of ordinary skill in the art. Compounds of formula (H) are prepared as described herein or may be prepared by methods known to one of ordinary skill in the art, such as those found in Great Britain Patent No. 1,334,705.

In general, compounds of formula (Ib) are prepared by first treating a suspension of a compound of formula (H) in an aprotic solvent mixture, such as methylene chloride and DMF, with a slightly excess molar amount of a peptide coupling reaction additive, such as 1-hydroxybenzotriazole ("HOBT") and a slightly excess molar amount a coupling agent for amide formation, such as 1-(3-dimethylaminopropyl)-3-ethylcarbodiimide ("EDCI") at ambient temperature. An equimolar amount of a compound of formula (D) in an aprotic solvent, such as methylene chloride, is then added to the reaction mixture. The reaction mixture is stirred at ambient temperature for a period of time of between about 4 hours and about 12 hours, preferably for a period of time of between about 6 hours and about 12 hours. The compound of formula (M) is then isolated from the reaction mixture by standard isolation techniques, such as evaporation of the solvents, extraction and concentration.

The compound of formula (M) is then treated under standard Williamson synthesis conditions, such as in the presence of base in an aprotic solvent, for example, cesium carbonate in acetonitrile:DMF, with an an equimolar amount of a compound of formula (J) at a temperature of between about ambient temperature and 100° C. The reaction mixture is stirred for a period of time of between 30 minutes and about 10 hours, preferably for abou 30 minutes. The compound of formula (Ib) is then isolated from the reaction mixture by standard isolation techniques, such as organic extraction and concentration.

If desired, compounds of formula (Ib) can be treated under standard hydrolysis conditions to yield the corresponding free amine or acid.

E. Preparation of Compounds of Formulae (Ic), (Id) and (Ie)

Compounds of formulae (Ic), (Id) and (Ie) are compounds of the invention and are prepared as described below in Reaction Scheme 5 wherein m, n, $R^1$, $R^2$ $R^4$, $R^5$ and $R^6$ are as described above in the Summary of the Invention, X is halo, $R^{3b}$ is aryl or aralkyl, and $R^{3c}$ is heteroaryl:

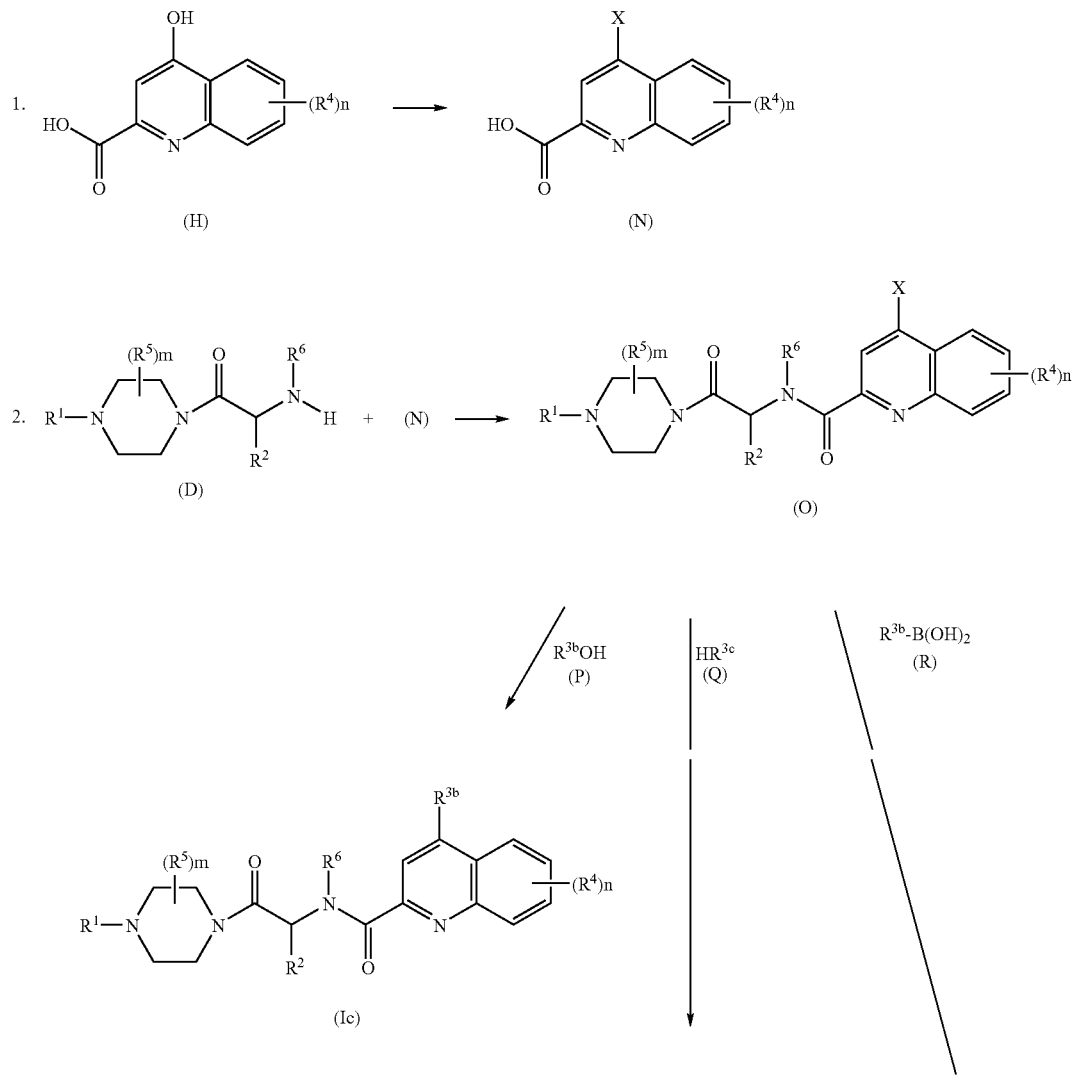

-continued

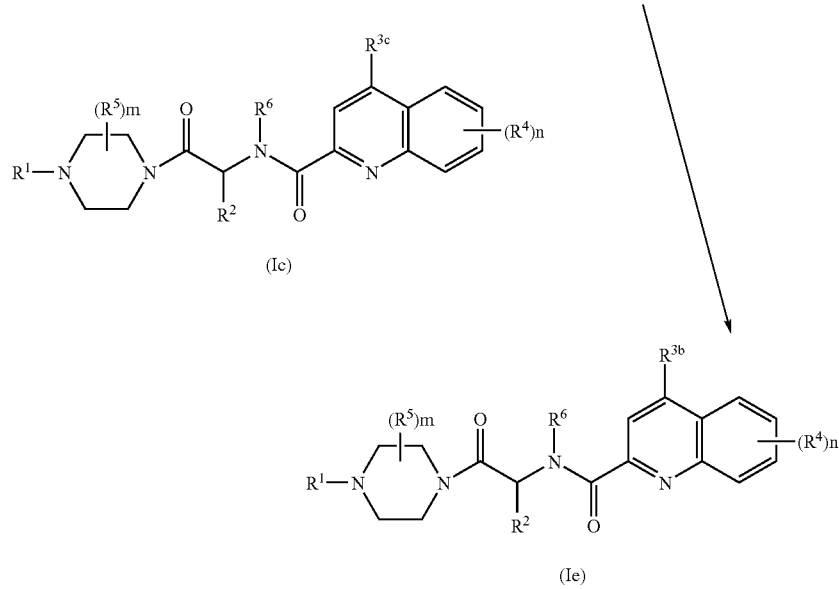

(Ic)

(Ie)

Compounds of formulae (H) and (D) are prepared as described herein or can be prepared according to methods known to one of ordinary skill in the art. Compounds of formulae (P), (Q) and (R) are commercially available, for example, from Aldrich Chemical Co., or can be prepared according to methods known to one of ordinary skill in the art.

In general, compounds of formulae (Ic), (Id) and (Ie) are prepared by first treating a compound of formula (H) with a halogenating agent, such as phosphorus pentachloride or phosphorus oxychloride, under standard halogenating conditions. The compound of formula (N) is isolated from the reaction mixture by standard isolation techniques.

The compound of formula (N) is then treated with a compound of formula (D) under standard peptide coupling conditions, as described herein, to yield a compound of formula (O), which is isolated from the reaction mixture by standard isolation techniques.

The compound of formula (O) in an polar aprotic solvent, such as DMSO, in the presence of a base, such as cesium carbonate, is then treated with a compound of formula (P). The resulting reaction mixture is heated to a temperature of between about 40° C. and about 60° C., preferably at about 60° C. for a period of time of between about 4 hours and about 16 hours, preferably for about 16 hours. The compound of formula (Ic) is then isolated from the reaction mixture by standard isolation techniques, such as filtration and purification by preparative HPLC. If desired, the compound of formula (Ic) can be treated under standard hydrolysis conditions to further yield the corresponding free acid or amine.

Alternatively, a mixture of a compound of formula (O) and a compound of formula (Q) in a polar aprotic solvent, such as DMSO, is heated to a temperature of between about 80° C. and 105° C., preferably to about 100° C., for a period of time of between about 6 hours and 18 hours, preferably for about 18 hours. The compound of formula (Id) is then isolated from the reaction mixture by standard isolation techniques, such as purification by reverse phase HPLC. If desired, the compound of formula (Id) can be hydrolyzed under standard hydrolysis conditions to further yield the corresponding amine or acid.

Alternatively, a compound of formula (O) is treated with a compound of formula (R) under standard boronic acid/ palladium coupling conditions to yield the corresponding compound of formula (Ie), which is isolated from the reaction mixture by standard isolation techniques. If desired, the compound of formula (Ie) can be hydrolyzed under standard hydrolysis conditions to further yield the corresponding amine or acid.

Alternatively, compounds of formula (Gb) may be used in the above Reaction Schemes in place of the compounds of formula (H).

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific preparations and examples are provided as a guide to assist in the practice of the invention, and are not intended as a limitation on the scope of the invention.

Preparation I

Compounds of formula (D)

A. To a solution of N-benzyloxycarbonyl-L-glutamic acid γ-t-butyl ester (24.4 g, 72.3 mmol) in tetrahydrofuran ("THF") (400 mL) and $CH_2Cl_2$ (100 mL) was added 1-hydroxybenzotriazole ("HOBT") (10.7 g, 79.5 mmol) and 1-(3-dimethylaminopropyl)-3-ethylcarbodiimide ("EDCI") (15.3 g, 79.5 mmol). After 5 minutes, 1-ethoxycarbonylpiperazine (11.7 mL, 79.5 mmol) was added and the reaction was stirred overnight. The reaction mixture was evaporated in vacuo to afford an oil, which was dissolved in ethyl acetate, and washed with saturated $NaHCO_3$, 1M $HaHSO_4$ and brine. The organic layer was evaporated in vacuo to 4-ethoxycarbonyl-1-(1-amino-3-(1,1-dimethylethoxycarbonyl)propyl)carbonylpiperazine (40.7 g), as an oil that was used without further purification. To 4-ethoxycarbonyl-1-(1-(benzyloxycarbonyl)amino-3-(1,1-dimethylethoxycarbonyl)propyl)carbonylpiperazine in MeOH (100 mL) was added 10% Pd/C (1 g) and the mixture was shaken under 50 psi $H_2$ overnight. The reaction was filtered and stripped to 4-ethoxycarbonyl-1-(1-amino-3-(1,1-dimethylethoxycarbonyl)propyl)carbonylpiperazine (25 g, 99%) and used without further purification; NMR (CDCl$_3$) 1.25 (t, 3), 1.43 (s, 9), 2.55 (m, 1), 1.90 (m, 1), 2.37 (m, 1), 2.55 (m, 1), 3.40–3.70 (m, 8), 3.80 (m, 1), 4.18 (q, 2) ppm.

B. In a similar manner, other compounds of formula (D) were prepared.

4-ethoxycarbonyl-1-(aminomethyl)carbonylpiperazine;
4-ethoxycarbonyl-1-(1-amino-3-carboxypropyl)carbonylpiperazine;
4-ethoxycarbonyl-2-methyl-1-(aminomethyl)carbonylpiperazine;
4-ethoxycarbonyl-3-methyl-1-(aminomethyl)carbonylpiperazine;
4-ethoxycarbonyl-1-(1-amino-5-((2-chlorobenzyloxy)carbonylamino)pentyl)carbonylpiperazine;
4-ethoxycarbonyl-1-(1-amino-2-(benzyloxycarbonyl)ethyl)carbonylpiperazine;
4-ethoxycarbonyl-1-(1-amino-2-phenylethyl)carbonylpiperazine;
4-ethoxycarbonyl-1-(1-amino-2-methylpropyl)carbonylpiperazine;
4-ethoxycarbonyl-1-(1-amino-2-carboxyethyl)carbonylpiperazine; and
4-ethoxycarbonyl-1-(1,5-diaminopentyl)carbonylpiperazine.

C. Alternatively, N-benzyloxycarbonyl-L-glutamic acid γ-t-butyl ester (34 g, 100 mmol) and EDCI (22 g, 110 mmol), HOBT (15 g, 110 mmol) were combined in 800 mL $CH_2Cl_2$ with triethylamine (24 mL, 172 mmol). The resulting reaction mixture was stirred at ambient temperature for 20 minutes, then 1-ethoxycarbonylpiperazine (18 g, 120 mmol) was added. The resulting mixture was stirred at ambient temperature for 15 hours. The reaction mixture was then washed with water, 2N NaHSO$_4$, and brine, then concentrated in vacuo to afford an oil, which was purified by flash column chromatography on silica gel (acetate/hexane=1/1) to afford 4-ethoxycarbonyl-1-(1-(benzyloxycarbonyl)amino-3-(1,1-dimethylethoxycarbonyl)propyl)carbonylpiperazine (40 g). 4-ethoxycarbonyl-1-(1-(benzyloxycarbonyl)amino-3-(1,1-dimethylethoxycarbonyl)propyl)carbonylpiperazine (40 g) was dissolved in 200 mL of MeOH, 2 g Pd/C(10%) was added and hydrogenated at 50 psi for 1 hour. Regular work up afforded 4-ethoxycarbonyl-1-(1-amino-3-(1,1-dimethylethoxycarbonyl)propyl)carbonylpiperazine (25 g).

Preparation 2

Compounds of formula (G)

A. To a solution of m-toludine (20.0 g, 0.186 mol) in methanol (300 mL), dimethyl acetylenedicarboxylate (26.42 g, 0.186 mol) was added drop-wise and the reaction mixture was stirred at ambient temperature for 30 minutes. The solvent was removed by evaporation and the residue was added to stirred diphenyl ether (150 ml), which has been preheated to 250° C. After 30 minutes, the mixture was cooled to ambient tempertature and the resulting precipitate was collected and washed with hot petroleum ether (1.5 L) to give a mixture (27.0 g) of 5-methyl-4-hydroxy-2-methoxycarbonylquinoline and 7-methyl-4-hydroxy-2-methoxycarbonylquinoline. The mixture was dissolved in boiling methanol (1.3 L) and kept at ambient temperature for two days to afford (6.45 g, 16%) of 7-methyl-4-hydroxy-2-methoxycarbonylquinoline, NMR (DMSO-d$_6$) 2.40 (s, 3), 3.92 (s, 3), 6.56 (s, 1), 7.16 (d, 1), 7.68 (s, 1), 7.94 (d, 1) ppm.

B. In a similar manner, other compounds of formula (G) were prepared as follows:
8-methoxy-4-hydroxy-2-methoxycarbonylquinoline;
5-amino-4-hydroxy-2-methoxycarbonylquinoline;
5-nitro-4-hydroxy-2-methoxycarbonylquinoline;
5-carboxymethylamino-4-hydroxy-2-methoxycarbonylquinoline;
7-chloro-4-hydroxy-2-methoxycarbonylquinoline;
5-di(acetyl)amino-4-hydroxy-2-methoxycarbonylquinoline;
5-acetylamino-4-hydroxy-2-methoxycarbonylquinoline;
5,7-dichloro-4-hydroxy-2-methoxycarbonylquinoline;
6-chloro-4-hydroxy-2-methoxycarbonylquinoline;
6-nitro-4-hydroxy-2-methoxycarbonylquinoline;
6-amino-4-hydroxy-2-methoxycarbonylquinoline;
7-benzyloxy-4-hydroxy-2-methoxycarbonylquinoline;
4,7-dihydroxy-2-methoxycarbonylquinoline;
7-prop-1-oxy-4-hydroxy-2-methoxycarbonylquinoline;
7-carboxymethoxy-4-hydroxy-2-methoxycarbonylquinoline;
7-diethylaminoethoxy-4-hydroxy-2-methoxycarbonylquinoline;
7-methoxy-4-hydroxy-2-methoxycarbonylquinoline;
7-(2-(4-hydroxy-2-carboxypyrrolidinyl)ethoxy)-4-hydroxy-2-methoxycarbonylquinoline;
8-methyl-4-hydroxy-2-methoxycarbonylquinoline;
6-diethylaminomethyl-4-hydroxy-2-methoxycarbonylquinoline;
6-benzyloxy-4-hydroxy-2-methoxycarbonylquinoline;
4,6-dihydoxy-2-methoxycarbonylquinoline;
6-carboxymethoxy-4-hydroxy-2-methoxycarbonylquinoline;
6-ethoxy-4-hydroxy-2-methoxycarbonylquinoline;
6-methoxy-4-hydroxy-2-methoxycarbonylquinoline;
6-prop-2-oxy-4-hydroxy-2-methoxycarbonylquinoline;
7-fluoro-4-hydroxy-2-methoxycarbonylquinoline;
7-trifluoromethyl-4-hydroxy-2-methoxycarbonylquinoline;
7-hydroxymethyl-4-hydroxy-2-methoxycarbonylquinoline;
7-cyano-4-hydroxy-2-methoxycarbonylquinoline;
7-nitro-4-hydroxy-2-methoxycarbonylquinoline;
6-carboxy-4-hydroxy-2-methoxycarbonylquinoline;
7-trifluoromethoxy-4-hydroxy-2-methoxycarbonylquinoline;
6-trifluoromethoxy-4-hydroxy-2-methoxycarbonylquinoline;
7-acetyl-4-hydroxy-2-methoxycarbonylquinoline;
5-ethoxycarbonyl-4-hydroxy-2-methoxycarbonylquinoline;
6-ethyl-4-hydroxy-2-methoxycarbonylquinoline;
7-carboxy-4-hydroxy-2-methoxycarbonylquinoline;
6-aminocarbonyl-4-hydroxy-2-methoxycarbonylquinoline;
6,7-dimethoxy-4-hydroxy-2-methoxycarbonylquinoline;
6-chloro-7-methyl-4-hydroxy-2-methoxycarbonylquinoline;
6-fluoro-7-methyl-4-hydroxy-2-methoxycarbonylquinoline;
6-fluoro-4-hydroxy-2-methoxycarbonylquinoline;
6-fluoro-7-chloro-4-hydroxy-2-methoxycarbonylquinoline;
7-bromo-4-hydroxy-2-methoxycarbonylquinoline;
6,7-dimethyl-4-hydroxy-2-methoxycarbonylquinoline;
6-methoxy-7-methyl-4-hydroxy-2-methoxycarbonylquinoline;

6-methoxy-7-chloro-4-hydroxy-2-methoxycarbonylquinoline;
6-chloro-8-fluoro-4-hydroxy-2-methoxycarbonylquinoline;
6,7-dichloro-4-hydroxy-2-methoxycarbonylquinoline;
6,8-difluoro-4-hydroxy-2-methoxycarbonylquinoline;
6,7-difluoro-4-hydroxy-2-methoxycarbonylquinoline;
6-dimethylamino-4-hydroxy-2-methoxycarbonylquinoline;
5-fluoro-6-methyl-4-hydroxy-2-methoxycarbonylquinoline;
6-methyl-7-chloro-4-hydroxy-2-methoxycarbonylquinoline;
6-acetyl-4-hydroxy-2-methoxycarbonylquinoline;
6-methylthio-4-hydroxy-2-methoxycarbonylquinoline;
4,5-dihydroxy-2-methoxycarbonylquinoline;
7-ethyl-4-hydroxy-2-methoxycarbonylquinoline;
5-methyl-4-hydroxy-2-methoxycarbonylquinoline;
5-hydroxymethoxy-4-hydroxy-2-methoxycarbonylquinoline;
5-(3-ethoxycarbonylpropoxy)-4-hydroxy-2-methoxycarbonylquinoline; and
5-(3-carboxypropoxy)-4-hydroxy-2-methoxycarbonylquinoline.

Preparation 3

Compounds of Formula (H)

A. 7-methyl-4-hydroxy-2-methoxycarbonylquinoline (6.45 g, 30.14 mmol) was suspended in MeOH (150 mL) and water (100 mL), and LiOH (3.08 g, 75.5 mmol) was added and stirred at ambient temperature for 2 hours. The methanol was evaporated in vacuo and residue was crystalized by addition of 2N hydrochloric acid. The resulting solid was filtered, washed with water and dried to afford 7-methyl-4-hydroxy-2-carboxyquinoline (6.0 g, 98%), NMR (DMSO-$d_6$) 2.40 (s, 3), 6.68 (s, 1), 7.22 (d, 1), 7.68 (s, 1), 7.96 (d, 1).

B. In a similar manner, the following compounds of formula (H) were prepared:
8-methoxy-4-hydroxy-2-carboxyquinoline;
5-amino-4-hydroxy-2-carboxyquinoline;
5-nitro-4-hydroxy-2-carboxyquinoline;
5-carboxymethylamino-4-hydroxy-2-carboxyquinoline;
7-chloro-4-hydroxy-2-carboxyquinoline;
5-di(acetyl)amino-4-hydroxy-2-carboxyquinoline;
5-acetylamino-4-hydroxy-2-carboxyquinoline;
5,7-dichloro-4-hydroxy-2-carboxyquinoline;
6-chloro-4-hydroxy-2-carboxyquinoline;
6-nitro-4-hydroxy-2-carboxyquinoline;
6-amino-4-hydroxy-2-carboxyquinoline;
7-benzyloxy-4-hydroxy-2-carboxyquinoline;
4,7-dihydroxy-2-carboxyquinoline;
7-prop-1-oxy-4-hydroxy-2-carboxyquinoline;
7-carboxymethoxy-4-hydroxy-2-carboxyquinoline;
7-diethylaminoethoxy-4-hydroxy-2-carboxyquinoline;
7-methoxy-4-hydroxy-2-carboxyquinoline;
7-(2-(4-hydroxy-2-carboxypyrrolidinyl)ethoxy)-4-hydroxy-2-carboxyquinoline;
8-methyl-4-hydroxy-2-carboxyquinoline;
6-diethylaminomethyl-4-hydroxy-2-carboxyquinoline;
3-methyl-4-hydroxy-2-carboxyquinoline;
6-benzyloxy-4-hydroxy-2-carboxyquinoline;
4,6-dihydoxy-2-carboxyquinoline;
6-carboxymethoxy-4-hydroxy-2-carboxyquinoline;
6-ethoxy-4-hydroxy-2-carboxyquinoline;
6-methoxy-4-hydroxy-2-carboxyquinoline;
6-prop-2-oxy-4-hydroxy-2-carboxyquinoline;
7-fluoro-4-hydroxy-2-carboxyquinoline;
7-trifluoromethyl-4-hydroxy-2-carboxyquinoline;
7-hydroxymethyl-4-hydroxy-2-carboxyquinoline;
7-cyano-4-hydroxy-2-carboxyquinoline;
7-nitro-4-hydroxy-2-carboxyquinoline;
2,6-dicarboxy-4-hydroxyquinoline;
7-trifluoromethoxy-4-hydroxy-2-carboxyquinoline;
6-trifluoromethoxy-4-hydroxy-2-carboxyquinoline;
7-acetyl-4-hydroxy-2-carboxyquinoline;
5-ethoxycarbonyl-4-hydroxy-2-carboxyquinoline;
6-ethyl-4-hydroxy-2-carboxyquinoline;
2,7-dicarboxy-4-hydroxyquinoline;
6-aminocarbonyl-4-hydroxy-2-carboxyquinoline;
6,7-dimethoxy-4-hydroxy-2-carboxyquinoline;
6-methyl-7-chloro-4-hydroxy-2-carboxyquinoline;
6-chloro-7-methyl-4-hydroxy-2-carboxyquinoline;
6-fluoro-7-methyl-4-hydroxy-2-carboxyquinoline;
6-fluoro-4-hydroxy-2-carboxyquinoline;
6-fluoro-7-chloro-4-hydroxy-2-carboxyquinoline;
7-bromo-4-hydroxy-2-carboxyquinoline;
6,7-dimethyl-4-hydroxy-2-carboxyquinoline;
6-methoxy-7-methyl-4-hydroxy-2-carboxyquinoline;
6-methoxy-7-chloro-4-hydroxy-2-carboxyquinoline;
6-chloro-8-fluoro-4-hydroxy-2-carboxyquinoline;
6,7-dichloro-4-hydroxy-2-carboxyquinoline;
6,8-difluoro-4-hydroxy-2-carboxyquinoline;
6,7-difluoro-4-hydroxy-2-carboxyquinoline;
6-dimethylamino-4-hydroxy-2-carboxyquinoline;
5-fluoro-6-methyl-4-hydroxy-2-carboxyquinoline;
6-acetyl-4-hydroxy-2-carboxyquinoline;
6-methylthio-4-hydroxy-2-carboxyquinoline;
4,5-dihydroxy-2-carboxyquinoline;
5-hydroxymethoxy-4-hydroxy-2-carboxyquinoline;
7-methyl-4-hydroxy-2-carboxyquinoline;
5-methyl-4-hydroxy-2-carboxyquinoline; 5-(3-ethoxycarbonylpropoxy)-4-hydroxy-2-carboxyquinoline; and
5-(3-carboxypropoxy)-4-hydroxy-2-carboxyquinoline.

Preparation 4

Compounds of formulae (Fb), (Ga) and (Gb)

A. To a solution of SnCl$_2$.H$_2$O (140 g, 0.62 mol) in ethanol (350 mL) was added a solution of 2,6-dichloro-3-nitrotoluene (25 g, 0.12 mol) in ethanol (50 mL). The reaction mixture was refluxed for 1 hour. The reaction mixture was concentrated under reduced pressure. The residue was dissolved in water (100 mL), pH was adjusted to approximately pH 12 with 1N NaOH solution and extracted with ethyl acetate. The ethyl acetate layer was washed with brine, dried over sodium sulfate, and concentrated to afford 2,6-dichloro-3-aminotoluene (21 g, 98%); NMR (CDCl$_3$) 2.42 (s, 3), 6.62 (d, 1), 7.14 (d, 1) ppm.

B. To a solution of 2,6-dichloro-3-aminotoluene (20.5 g, 0.11 mol) in methanol (300 mL) was added dimethyl acetylenedicarboxylate (15 mL, 0.12 mol) and the reaction mixture was refluxed for 2 hours. The reaction mixture was concentrated under reduced pressure to a yellow solid. Diphenyl ether (350 mL) was heated to 230–240° C., and the yellow solid was added to it. The temperature was maintained at 230–240° C. for 20 minutes and the reaction mixture was cooled slowly to ambient temperature and diluted with petroleum ether (1L). The solid was filtered and washed with hot ethyl acetate to afford a brown solid, 2-(methoxycarbonyl)-4-oxo-6,8-dichloro-7-methylquinoline (28.5 g, 85%); NMR (CDCl$_3$) 2.62 (s, 3), 4.04 (s, 3), 7.02 (s, 1), 8.24 (s, 1) ppm.

C. 2-(Methoxycarbonyl)-4-oxo-6,8-dichloro-7-methylquinoline (28.5 g, 99.6 mmol) was suspended in methanol (1 L) and a solution of LiOH.H$_2$O (20.5 g, 0.5 mol) in water (200 mL) was added to the solution. The resulting reaction mixture was stirred at ambient temperature for 0.5 hours. Pd/C (5.8 g) was added to the reaction mixture and the resulting reaction mixture was shaken under 50 Psi hydrogen overnight. The reaction mixture was filtered, concentrated under reduced pressure to remove methanol, diluted with water (300 mL) and the pH was adjusted to between pH 3 and pH 4 by 2N HCl. The precipitate was collected by filtration, washed with water and dried to afford a white solid, 2-carboxy-4-oxo-7-methylquinoline (20 g, 90%); NMR (DMSO-d$_6$) 2.40 (s, 3), 6.60 (s, 1), 7.20 (d, 1), 7.68 (s, 1), 7.96 (d, 1) ppm.

D. Alternatively, to a solution of 4-chloro-3-methyl aniline (20.0 g, 0.141 mol) in MeOH (400 mL) was added drop-wise dimethyl acetylenedicarboxylate (21.07 g, 0.148 mol). The reaction mixture was stirred at ambient temperature for 30 minutes. The solvent was removed by evaporation and the residue was added to stirred diphenyl ether (300 mL), which has been preheated to 250° C. After 30 minutes, the mixture was cooled to ambient temperature and the resulting precipitate was collected and washed with 1 L of hot petroleum ether to give a mixture (29.0 g) of 2-methoxycarbonyl-6-chloro-7-methyl-4-oxoquinoline and 2-methoxycarbonyl-6-chloro-5-methyl-4-oxoquinoline as a gray solid. The mixture was dissolved in boiling methanol (1 L) and filtered hot. The collected solids were boiled in 1.2 L of methanol and filtered hot to afford (6.45 g, 16%) of 2-methoxycarbonyl-6-chloro-7-methyl-4-oxoquinoline: $^1$H NMR (DMSO-d$_6$) 2.41 (s, 3), 3.92 (s, 3), 6.58 (s, 1), 7.86 (s, 1), 7.96 (s, 1) ppm.

E. 2-Methoxycarbonyl-6-chloro-7-methyl-4-oxoquinoline (7.00 g, 28.00 mmol) was suspended in 300 mL of MeOH and 100 mL of water. Lithium hydroxide (3.40 g, 90 mmol) was added and the reaction was stirred at room temp for 2 hours. The methanol was evaporated in vacuo and the product was crystallized by addition of 2N hydrochloric acid. The solid was filtered, washed with water and dried to afford 5.9 g (88%) of 2-carboxy-6-chloro-7-methyl-4-oxoquinoline: H NMR (DMSO-d$_6$) 2.40 (s, 3), 6.60 (s, 1), 7.84 (s, 1), 7.98 (s, 1) ppm.

Preparation 5

Compounds of Formulae (K) and (L)

A. 2-carboxy-4-hydroxyquinoline (5 g, 1.0 eq) was dissolved in 50 mL DMF. Cesium carbonate (20 g, 2.3 eq) was added to the solution and the resulting reaction mixture was heated at 50° C. for 20 minutes. Benzyl bromide (10 g, 2.1 eq) was added. The resulting reaction mixture was stirred at 50° C. for 1 hour. Then the reaction mixture was poured into 500 mLice-water, the precipitate was collected by filtration, and dried in vacuo to afford 2-benzyloxycarbonyl-4-benzyloxyquinoline (9.1 g). 2-benzyloxycarbonyl-4-benzyloxyquinoline (9.0 g) was dissolved in 50 mL THF, and 2 N LiOH solution (20 mL) was added, and the resulting reaction mixture was stirred at ambient temperature for 2 hours. The solvent was then removed in vacuo, and the residue acidified by the addition of 2N NaHSO$_4$ to pH 3–4. The white precipitate was collected to afford 2-carboxy-4-benzyloxyquinoline (7.2 g), which was used without further purification.

B. In a similar manner, other compounds of formula (K) and (L) were prepared.

Preparation 6

Compounds of Formula (M)

A. To a suspension of 2-carboxy-6-chloro-7-methyl-4-oxoquinoline (7.5 g, 31.69 mmol) in dichloromethane:DMF (350 mL, 2.5:1) was added HOBT (5.13 g, 38 mmol) and EDCI (7.25 g, 38 mmol) and the reaction mixture was stirred for 10 minutes. A solution of 4-ethoxycarbonyl-1-(1-amino-3-(1,1-dimethylethoxycarbonyl)propyl)carbonylpiperazine (10.8 g, 31.64 mmol) in 50 mL dichloromethane was added. The reaction was stirred at ambient temperature for 6 hours. The solvent was evaporated in vacuo and the residue was partitioned in ethyl acetate and water. The aqueous layer was extracted with ethyl acetate. The combined organic layers were washed with water, brine and concentrated to afford an off-white foam that was purified by flash chromatography (2% methanol in dichloromethane) to afford 2-[1S-(4-(ethoxycarbonyl)piperazin-1-yl)carbonyl-3-(1,1-dimethylethoxycarbonyl)propyl]aminocarbonyl-7-methyl-6-chloro-4-hydroxyquinoline as a white foam, (14.4 g, 80%).

B. In a similar manner, other compounds of formula (M) were prepared.

C. Alternatively, 2-carboxy-4-hydroxyoxoquinoline (640 mg, 3.2 mmol), EDCI (674 mg, 3.5 mmol), and HOBT (525 mg, 3.5 mmol) were combined in 20 mL CH$_2$Cl$_2$ with triethylamine (0.67 mL, 4.8 mmol). The resulting reaction mixture was stirred at ambient temperature for 10 minutes, then 4-ethoxycarbonyl-1-(1-amino-3-(1,1-dimethylethoxycarbonyl)propyl)-carbonylpiperazine (1.1 g, 3.3 mmol) was added. The resulting mixture was stirred at ambient temperature for 2 hours. The reaction mixture was washed with water, 2N NaHSO$_4$, and brine, then concentrated in vacuo to afford an oil, which was purified by flash column chromatography on silica gel to afford 2-[1S-(4-(ethoxycarbonyl) piperazin-1-yl)carbonyl-3-(1,1-dimethylethoxycarbonyl) propyl]aminocarbonyl-4-hydroxyquinoline (1.28 g).

D. Alternatively, to a solution of 2-carboxy-6-chloro-8-fluoro-4-hydroxyquinoline (1.09, 4.14 mmol) in DMF (50 mL) was added diisopropylethyl amine (3.0 eq., 2.2 mL). The mixture was stirred at ambient temperature for 30 minutes. EDCI (1.2 eq., 969 mg) and HOBT (1.1 eq., 628 mg) were added, followed by the addition of 4-ethoxycarbonyl-1-(1-amino-3-(1,1-dimethylethoxycarbonyl)propyl) carbonylpiperazine (1.493 g, 1.05 eq.) and the mixture was stirred overnight at ambient temperature. The solvent, DMF, was evaporated in vacuo to afford a crude product, which was dissolved in ethyl acetate, washed with saturated NaHCO$_3$, 1M NaHSO$_4$ and brine. The organic layer was evaporated. Flash column chromatography with 1%–3% MeOH in CH$_2$Cl$_2$ afforded the coupling product, 2-[1S-(4-(ethoxycarbonyl)piperazin-1-yl)carbonyl-3-(1,1-dimethylethoxycarbonyl)propyl]aminocarbonyl-6-chloro-8-fluoro-4-hydroxyquinoline in acetic acid, (2.01 g).

Preparation 7

Compounds of Formula (N)

A. To 20 mL POCl$_3$ was added 2-carboxy-7-methyl-4-hydroxyquinoline (2.5 g, 12.3 mmol) and PCl$_5$ (11.5 g, 55 mmol). The mixture was heated to 130° C. for 3 hours. The reaction mixture was cooled and poured onto ice. The solution was neutralized with solid NaOH and adjusted to pH 11 with solid KOH. The tan precipitate was filtered, slurried in 250 mL water and adjusted to pH 2 with concentrated HCl. The resultant solid was filtered and dried to afford 2-carboxy-7-methyl-4-chloroquinoline (1.34 g, 50%).

B. In a similar manner, other compounds of formula (N) were prepared:

Preparation 8

Compounds of Formula (O)

A. A solution of 4-ethoxycarbonyl-1-(1-amino-3-(methoxycarbonyl)propyl)carbonylpiperazine (0.97 g, 3.23 mmol), 4-chloro-2-carboxyquinoline (0.67 g, 3.23 mmol), EDCI (0.68 g, 3.55 mmol) and HOBT (0.48 g, 3.55 mmol) was combined in 30 mL of THF. The reaction mixture was stirred overnight at ambient temperature. The reaction was diluted with ethyl acetate and washed with water. The organic layer was concentrated to give a dark oil (0.87 g) that was purified by flash chromotography through silica gel with 2:1 ethyl acetate-hexanes to provide 2-[1S-(4-(ethoxycarbonyl)piperazin-1-yl)carbonyl-3-(methoxycarbonyl)propyl]aminocarbonyl-4-chloroquinoline, (0.46 g).

B. A solution of 2-[1S-(4-(ethoxycarbonyl)piperazin-1-yl)carbonyl-3-(methoxycarbonyl)propyl]aminocarbonyl-4-chloroquinoline (0.15 g, 0.313 mmol) was dissolved in 5 mL THF and LiOH (0.25 M, 1.9 mL, 0.47 mmol) was added. The reaction was stirred for 2 hours. The reaction was concentrated to an oil, acidified with 10% HCl, extracted into ethyl acetate, and concentrated to provide pure 2-[1S-(4-(ethoxycarbonyl)piperazin-1-yl)carbonyl-3-carboxypropyl]aminocarbonyl-4-chloroquinoline (167 mg): $^1$H NMR 1.20 (t, 3), 1.90 (m, 1), 2.05 (m, 1), 2.35 (m, 2), 3.35–3.60 (m, 8), 3.65 (m, 2), 4.05 (q, 2), 5.07 (m, 1), 7.95 (m, 1), 8.02 (m, 1), 8.23 (s, 1), 8.30 (m, 1), 8.98 (m, 1) ppm.

C. Alternatively, to a solution of 2-carboxy-7-methyl-4-chloroquinoline (1.3 g, 5.9 mmol) in THF (50 mL) at 0° C. was added N-methylmorpholine (1.7 mL, 14.7 mmol) followed by iso-butylchloroformate (0.84 mL, 6.45 mmol). The reaction was stirred for 0.5 hours, then 4-ethoxycarbonyl-1-(1-amino-3-(1,1-dimethylethoxycarbonyl)propyl)carbonylpiperazine (2.0 g, 5.9 mmol) was added and the reaction was warmed to ambient temperature. Aqueous work-up afforded a crude product. The sample was purified by flash chromatography through silica gel (3:2 ethyl acetate:hexanes) to afford 2-[1S-(4-(ethoxycarbonyl)piperazin-1-yl)carbonyl-3-(1,1-dimethylethoxycarbonyl)propyl]aminocarbonyl-7-methyl-4-chloroquinoline (0.95 g, 30%).

D. In a similar manner, other compounds of formula (O) were prepared:

EXAMPLE 1

Compounds of Formula (Ia)

A. 2-Carboxy-4-benzyloxyquinoline (800 mg, 1.0 eq) and EDCI (680 mg, 1.1 eq), HOBT (520 mg, 1.1 eq) were combined in 25 mL methylene chloride with triethylamine (1.0 mL, 3.2 eq). The resulting reaction mixture was stirred at ambient temperature for 10 minutes, and then 4-ethoxycarbonyl-1-(1-amino-3-(benzyloxycarbonyl)propyl)carbonylpiperazine was added (1.0 g, 1.25 eq). The resulting reaction mixture was stirred at ambient temperature for 12 hours. The reaction mixture was then washed with water, 2N NaHSO$_4$, and brine, then concentrated in vacuo to afford an oil, which was purified by flash column chromatography on silica gel to afford 2-[1S-(4-(ethoxycarbonyl)piperazin-1-yl)carbonyl-3-benzyloxycarbonylpropyl]aminocarbonyl-4-benzyloxyquinoline (1.6 g). Then 50 mg of 2-[1S-(4-(ethoxycarbonyl)piperazin-1-yl)carbonyl-3-benzyloxycarbonylpropyl]aminocarbonyl-4-benzyloxyquinoline was dissolved in 2 mL MeOH and 1 mL water, and lithium hydroxide added (10 mg), and the resulting mixture was stirred at ambient temperature for 2 hours. Standard work-up afforded 2-[1S-(4-(ethoxycarbonyl)piperazin-1-yl)carbonyl-3-carboxypropyl]aminocarbonyl-4-benzyloxyquinoline (30 mg).

B. In a similar manner, the following compounds of formula (Ia) were prepared:

2-[(4-(ethoxycarbonyl)piperazin-1-yl)carbonylmethyl]aminocarbonyl-4-benzyloxyquinoline;

2-[(4-(ethoxycarbonyl)piperazin-1-yl)carbonylmethyl]aminocarbonyl-6-fluoro-7-methyl-4-(1-phenyl-1-carboxy)methoxyquinoline;

2-[1-(4-(ethoxycarbonyl)piperazin-1-yl)carbonyl-3-benzyloxycarbonylpropyl]aminocarbonyl-4-benzyloxy-8-methoxyquinoline; and 2-[1S-(4-(ethoxycarbonyl)piperazin-1-yl)carbonyl-3-carboxypropyl]aminocarbonyl-4-benzyloxy-8-methoxyquinoline.

EXAMPLE 2

Compounds of Formula (Ib)

A. Methyl α-bromophenylacetate (0.22 g, 1 mmol) was added to a solution of 2-[1S-(4-(ethoxycarbonyl)piperazin-1-yl)carbonyl-3-(1,1-dimethylethoxycarbonyl)propyl]-aminocarbonyl-7-methyl-6-chloro-4-hydroxyquinoline (0.42 g, 0.74 mmol) and cesium carbonate (0.48 g, 1.48 mmol) in 10 mL CH$_3$CN/DMF (4:1) and stirred at 40° C. for 30 minutes. The reaction mixture was filtered, evaporated, dissolved in ethyl acetate, washed with water, brine and concentrated to afford 2-[1S-(4-(ethoxycarbonyl)piperazin-1-yl)carbonyl-3-(1,1-dimethylethoxycarbonyl)propyl]aminocarbonyl-7-methyl-6-chloro-4-(1-phenyl-1-methoxycarbonyl)methoxyquinoline as a reddish oil (0.55 g). The crude material was carried on to the next step.

B. A solution of 2-[1S-(4-(ethoxycarbonyl)piperazin-1-yl)carbonyl-3-(1,1-dimethylethoxycarbonyl)propyl]aminocarbonyl-7-methyl-6-chloro-4-(1-phenyl-1-methoxycarbonyl)methoxyquinoline (0.55 g) in MeOH (5 mL) was saponified by reaction with LiOH (3 mL, 0.25 M) for 40 minutes. The solvent was evaporated and the residue was purified by preparative HPLC to afford 2-[1S-(4-(ethoxycarbonyl)piperazin-1-yl)carbonyl-3-(1,1-dimethylethoxycarbonyl)propyl]aminocarbonyl-7-methyl-6-chloro-4-(1-phenyl-1-carboxy)methoxyquinoline as two pure diastereomers (A) and (B) as white solids (A 180 mg, B 190 mg): $^1$H NMR of B (DMSO-d$_6$) 1.18 (t, 3), 1.20 (s, 9), 1.82 (m, 1), 2.0 (m, 1), 2.22 (m, 2), 2.54 (s, 3), 3.46 (m, 8), 4.04 (q, 2), 5.00 (m, 1), 6.38 (s, 1), 7.2 (m, 3), 7.45 (s, 1), 7.62 (m, 2), 8.04 (s, 1), 8.10 (s, 1), 8.86 (d, 1) ppm.

C. A solution of 2-[1S-(4-(ethoxycarbonyl)piperazin-1-yl)carbonyl-3-(1,1-dimethylethoxycarbonyl)propyl]aminocarbonyl-7-methyl-6-chloro-4-(1-phenyl-1-carboxy)methoxyquinoline (190 mg, 0.23 mmol) in 50% TFA-dichloromethane (6 mL) was stirred at ambient temperature for 1 hour. The solvent was evaporated and purified by preparative HPLC to afford 2-[1S-(4-(ethoxycarbonyl)piperazin-1-yl)carbonyl-3-carboxypropyl]aminocarbonyl-7-methyl-6-chloro-4-(1-phenyl-1-carboxy)methoxyquinoline in trifluoroacetic acid; as a white solid (116 mg, 66%) as a TFA salt: $^1$H NMR (DMSO-d$_6$) 1.12 (t, 3), 1.85 (m, 1), 2.05 (m, 1), 2.30 (m, 2), 2.55 (s, 3), 3.45 (m, 6), 3.65 (m, 2), 4.05

(q. 2), 5.02 (m, 1), 6.39 (s, 1), 7.45 (m, 3), 7.56 (s, 1), 7.69 (d, 2), 8.10 (s, 1), 8.20 (s, 1) 8.88 (d, 1) ppm.

D. Alternatively, 2-[1S-(4-(ethoxycarbonyl)piperazin-1-yl)carbonyl-3-(1,1-dimethylethoxycarbonyl)propyl]aminocarbonyl-4-hydroxyquinoline (100 mg, 1.0 eq) and cesium carbonate (190 mg, 3.0 eq.) were combined in 5 mL of DMF, and methyl α-bromophenylacetate (66 mg, 1.5 e q) was added. The resulting reaction mixture was stirred at 50° C. for 1 hour. Then the mixture was poured into 50 mL ice-water, extracted with 2×50 ml ethyl acetate, and the organic phase was washed with 3×30 ml water, and then brine. The crude product was purified by flash column chromatography (acetate/gexane=1/1) to provide 2-[1S-(4-(ethoxycarbonyl)piperazin-1-yl)carbonyl-3-(1,1-dimethylethoxycarbonyl)propyl]-aminocarbonyl-4-(1-phenyl-1-methoxycarbonyl)methoxyquinoline (120 mg), which was dissolved in 2 mL of trifluoroacetic acid. The resulting reaction mixture was stirred at ambient temperature for 20 minutes, and then concentrated in vacuo. The residual oil was dissolved in mL ethyl acetate, washed with saturated $NaHCO_3$, brine, and dried in vacuo to afford (90 mg). 2-[1S-(4-(ethoxycarbonyl)piperazin-1-yl)carbonyl-3-carboxypropyl]aminocarbonyl-4-(1-phenyl-1-methoxycarbonyl)methoxyquinoline (60 mg) in 3 mL MeOH was added to a solution of 15 mg (3 eq.) LiOH in 2 mL water. The resulting reaction mixture was stirred at ambient temperature for 2 hours. then the MeOH solvent was removed in vacuo. The pH was adjusted to pH 3–4 with 2 N $NaHSO_2$, and extracted by 2×20 mL acetate to afford a white solid, 2-[1S-(4-(ethoxycarbonyl)piperazin-1-yl)carbonyl-3-carboxypropyl]aminocarbonyl-4-(1-phenyl-1-carboxy)methoxyquinoline (40 mg).

E. In a similar manner, the following compounds of formula (Ib) were prepared:

2-[1S-(4-(3-methylphenyl)piperazin-1-yl)carbonyl-3-(1,1-dimethylethoxycarbonyl)propyl]aminocarbonyl-4-benzyloxyquinoline;

2-[1S-(4-(3-methylphenyl)piperazin-1-yl)carbonyl-3-carboxypropyl]aminocarbonyl-4-benzyloxyquinoline;

2-[1S-(4-(ethoxycarbonyl)piperazin-1-yl)carbonyl-3-carboxypropyl]aminocarbonyl-7-methyl-4-(1-phenyl-1-carboxy)methoxyquinoline;

2-[1S-(4-(ethoxycarbonyl)piperazin-1-yl)carbonyl-3-carboxypropyl]aminocarbonyl-6-fluoro-7-methyl-4-(1-phenyl-1-carboxy)methoxyquinoline;

2-[1S-(4-(ethoxycarbonyl)piperazin-1-yl)carbonyl-3-carboxypropyl]aminocarbonyl-7-chloro-4-(1-carboxy-1-phenyl)methoxyquinoline in trifluoroacetic acid;

2-[1S-(4-(ethoxycarbonyl)piperazin-1-yl)carbonyl-3-carboxypropyl]aminocarbonyl-6-fluoro-7-methyl-4-(1-naphth-1-yl-1-carboxy)methoxyquinoline;

2-[1S-(4-(ethoxycarbonyl)piperazin-1-yl)carbonyl-3-carboxypropyl]aminocarbonyl-7-methyl-6-fluoro-4-(1-carboxy-1-(2-fluoro)phenyl)methoxyquinoline in trifluoroacetic acid;

2-[1S-(4-(ethoxycarbonyl)piperazin-1-yl)carbonyl-3-carboxypropyl]aminocarbonyl-7-methyl-4-(1-ethoxycarbonyl-1-phenyl)methoxyquinoline in trifluoroacetic acid;

2-[1S-(4-(ethoxycarbonyl)piperazin-1-yl)carbonyl-3-carboxypropyl]aminocarbonyl-4-(5-methylisoxazol-3-yl)methoxyquinoline in trifluoroacetic acid;

2-[1S-(4-(ethoxycarbonyl)piperazin-1-yl)carbonyl-3-carboxypropyl]aminocarbonyl-4-(2-methylthiazol-4-yl)methoxyquinoline in trifluoroacetic acid;

2-[1S-(4-(ethoxycarbonyl)piperazin-1-yl)carbonyl-3-methoxycarbonylpropyl]aminocarbonyl-4-(1-phenyl-1-ethoxycarbonyl-1-chloro)methoxyquinoline;

2-[1S-(4-(ethoxycarbonyl)piperazin-1-yl)carbonyl-3-carboxypropyl]aminocarbonyl-6,8-difluoro-4-(1-carboxy-1-phenyl)methoxyquinoline in trifluoroacetic acid;

2-[1S-(4-(ethoxycarbonyl)piperazin-1-yl)carbonyl-3-carboxypropyl]aminocarbonyl-7-chloro-6-methyl-4-(1-phenyl-1-carboxy)methoxyquinoline in trifluoroacetic acid;

2-[1-(4-(ethoxycarbonyl)piperazin-1-yl)carbonyl-3-carboxypropyl]aminocarbonyl-7-methyl-6-fluoro-4-(1-carboxy-1-thien-3-yl)methoxyquinoline in trifluoroacetic acid;

2-[1S-(4-(ethoxycarbonyl)piperazin-1-yl)carbonyl-3-carboxypropyl]aminocarbonyl-6-chloro-7-methyl-4-(5-methylisoxazol-3-yl)methoxyquinoline;

2-[1-(4-(ethoxycarbonyl)piperazin-1-yl)carbonyl-3-carboxypropyl]aminocarbonyl-6-chloro-7-methyl-4-(2-methylthiazol-4-yl)methoxyquinoline in trifluoroacetic acid;

2-[1S-(4-(ethoxycarbonyl)piperazin-1-yl)carbonyl-3-carboxypropyl]aminocarbonyl-7-methyl-6-fluoro-4-(1-carboxy-1-(4-chloro)phenyl)methoxyquinoline in trifluoroacetic acid;

2-[1S-(4-(ethoxycarbonyl)piperazin-1-yl)carbonyl-3-carboxypropyl]aminocarbonyl-7-methyl-6-fluoro-4-(1-carboxy-1-(3-methoxy)phenyl)methoxyquinoline in trifluoroacetic acid;

2-[1S-(4-(ethoxycarbonyl)piperazin-1-yl)carbonyl-3-carboxypropyl]aminocarbonyl-6-dimethylamino-4-(1-phenyl-1-carboxy)methoxyquinoline;

2-[1S-(4-(1,1-dimethylethoxycarbonyl)piperazin-1-yl)carbonyl-3-carboxypropyl]aminocarbonyl-6-fluoro-7-methyl-4-(1-phenyl-1-carboxy)methoxyquinoline;

2-[(4-(ethoxycarbonyl)piperazin-1-yl)carbonylmethyl]aminocarbonyl-6-fluoro-7-methyl-4-(1-phenyl-1-carboxy)methoxyquinoline;

2-[1S-(4-(3-methylphenyl)piperazin-1-yl)carbonyl-3-(1,1-dimethylethoxycarbonyl)propyl]aminocarbonyl-6-fluoro-7-methyl-4-(1-phenyl-1-carboxy)methoxyquinoline;

2-[1S-(4-(3-methylphenyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(1,1-dimethylethoxycarbonyl)piperazin-1-yl)carbonyl-3-methoxycarbonylpropyl]aminocarbonyl-6-fluoro-7-methyl-4-(1-phenyl-1-carboxy)methoxyquinoline;

2-[1S-(4-(1,1-dimethylethoxycarbonyl)piperazin-1-yl)carbonyl-3-carboxypropyl]aminocarbonyl-6-fluoro-7-methyl-4-(1-phenyl-1-carboxy)methoxyquinoline;

2-[1S-(4-(furan-2-ylcarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(methoxycarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(1,1-dimethylethylaminocarbonyl)piperazin-1-yl)carbonyl-3-carboxypropyl]aminocarbonyl-6-fluoro-7-methyl-4-(1-phenyl-1-carboxy)methoxyquinoline in trifluoroacetic acid;

2-[1S-(4-(phenyl)piperazin-1-yl)carbonyl-3-(1,1-dimethylethoxycarbonyl)propyl]aminocarbonyl-6-fluoro-7-methyl-4-(1-phenyl-1-carboxy)methoxyquinoline; and 2-[1S-(4-(phenyl)piperazin-1-yl)carbonyl-3-carboxypropyl]aminocarbonyl-6-fluoro-7-methyl-4-(1-phenyl-1-carboxy)methoxyquinoline in trifluoroacetic acid.

E. Alternatively, 2-[(4-(ethoxycarbonyl)piperazin-1-yl)carbonylmethyl]aminocarbonyl-4-hydroxyquinoline (100 mg, 1.0 eq) and cesium carbonate (300 mg, 2.5 eq) were combined in 10 mL of DMF. Methyl 4-(bromomethyl)benzoate (65 mg, 1.1 eq) was added to the solution and the resulting mixture was stirred at 50° C. for 30 minutes. The reaction mixture was poured into 200 mL of ice water, extracted with 2×100 mL ethyl acetate, and the organic phase was washed with 3×100 mL water, followed by a brine wash. The crude mixture was purified by flash column chromatography to provide 2-[(4-(ethoxycarbonyl)piperazin-1-yl)carbonylmethyl]aminocarbonyl-4-(4-methoxycarbonyl)benzyloxyquinoline (107 mg). To a solution of 2-[(4-(ethoxycarbonyl)piperazin-1-yl)carbonylmethyl] aminocarbonyl-4-(4-methoxycarbonyl)benzyloxyquinoline (78 mg) in 4 mL THF was added a solution of 16 mg LiOH in 3 mL of water. The resulting reaction mixture was stirred at ambient temperature for 2 hours, followed by standard work-up to provided 65 mg of 2-[(4-(ethoxycarbonyl)piperazin-1-yl)carbonylmethyl]aminocarbonyl-4-(4-carboxy)benzyloxyquinoline.

F. In a similar manner, the following compounds of formula (Ib) were prepared:

2-[(4-(ethoxycarbonyl)piperazin-1-yl)carbonylmethyl]aminocarbonyl-4-(3-methoxycarbonyl)benzyloxyquinoline; and 2-[(4-(ethoxycarbonyl)piperazin-1-yl)carbonylmethyl]aminocarbonyl-4-(3-carboxy)benzyloxyquinoline.

G. Alternatively, to a suspension of NaH (53.0 mg, 2.20 mmol), DMF (8 mL) was added a solution of 2-[1S-(4-(ethoxycarbonyl)piperazin-1-yl)carbonyl-3-(1,1-dimethylethoxycarbonyl)propyl]aminocarbonyl-6-chloro-8-fluoro-4-hydroxyquinoline (500 mg, 0.88 mmol) in DMF (2 mL). The reaction mixture was stirred at ambient temperature for 30 minutes. A solution of methyl α-bromophenylacetate (4 eq., 831 mg) in DMF (3 mL) was added dropwise and the reaction mixture was heated at 50° C. overnight. The solvent, DMF, was evaporated in vacuo. The residue was treated with ethyl acetate, washed with water (2×) and brine, followed by evaporation and flash column chromatography with 1–2% MeOH in DCM to afford 2-[1S-(4-(ethoxycarbonyl)piperazin-1-yl)carbonyl-3-(1,1-dimethylethoxycarbonyl)propyl]aminocarbonyl-6-chloro-8-fluoro-4-(1-methoxycarbonyl-1-phenyl)methoxyquinoline (324 mg). 2-[1S-(4-(Ethoxycarbonyl)piperazin-1-yl)carbonyl-3-(1,1-dimethylethoxycarbonyl)propyl]aminocarbonyl-6-chloro-8-fluoro-4-(1-methoxycarbonyl-1-phenyl)methoxyquinoline (324 mg, 0.45 mmol) was then treated with TFA: DCM (1:1, 1.8 mL) at ambient temperature for 4 hours. Evaporation, dilution with DCM, and repeated evaporation gave a crude product. Flash column chromatography with 100% ethyl acetate and 3–5% MeOH (with 0.1% acetic acid) in ethyl acetate afforded 2-[1S-(4-(ethoxycarbonyl)piperazin-1-yl)carbonyl-3-carboxypropyl]aminocarbonyl-6-chloro-8-fluoro-4-(1-methoxycarbonyl-1-phenyl)methoxyquinoline in acetic acid; (233 mg): NMR (CD$_3$OD) 1.25 (t, 3),1.99 (m, 1), 2.2 (m, 1), 2.45 (m, 2), 3.4–3.8 (m, 11), 4.16 (q, 2), 5.25 (m, 1), 6.38 (s, 1), 7.45 (m, 3), 7.68 (m, 4), 8.10 (s, 1), 9.05 (m, 1) ppm.

H. 2-[1S-(4-(Ethoxycarbonyl)piperazin-1-yl)carbonyl-3-carboxypropyl]aminocarbonyl-6-chloro-8-fluoro-4-(1-methoxycarbonyl-1-phenyl)methoxyquinoline (154 mg, 0.233 mmol) was added to a mixture of THF:H$_2$O, 3: 1, 6.0 mL) and LiOH (4 eq.). The mixture was stirred at ambient temperature for 1.5 hours. The pH value was adjusted to 3.0 with 1N HCl solution, followed by extraction with ethyl acetate and evaporation of solvent to give a crude product. Flash column chromatography with 100% ethyl acetate and 5–10% MeOH (with 0.1% AcOH) in ethyl acetate afforded 2-[1S-(4-(ethoxycarbonyl)piperazin-1-yl)carbonyl-3-carboxypropyl]aminocarbonyl-6-chloro-8-fluoro-4-(1-carboxy-1-phenyl)methoxyquinoline in acetic acid (30 mg): NMR (CD$_3$OD) 1.25 (t, 3), 1.99 (m, 1), 2.2 (m, 1), 2.45 (m, 2), 3.4–3.9 (m, 8), 4.16 (q, 2), 5.20 (m, 1), 6.35 (s, 1), 7.45–7.75 (m, 7), 8.05 (s, 1), 9.02 (m, 1) ppm.

EXAMPLE 3

Compounds of Formulae (Ic), (Id) and (Ie)

A. To a mixture of 2-[1S-(4-(ethoxycarbonyl)piperazin-1-yl)carbonyl-3-(1,1-dimethylethoxycarbonyl)propyl]aminocarbonyl-7-methyl-4-chloroquinoline (475 mg, 0.87 mmol) and CsCO$_3$ (1.13 g, 4 mmol) in 20 mL DMSO was added methyl 3-hydroxybenzoate (160 mg, 1 mmol). The reaction was heated at 60° C. overnight. The reaction was filtered and purified by preparative HPLC to afford 2-[1S-(4-(ethoxycarbonyl)piperazin-1-yl)carbonyl-3-(1,1-dimethylethoxycarbonyl)propyl]aminocarbonyl-7-methyl-4-(3-methoxycarbonyl)-phenoxyquinoline (200 mg, 35%).

B. 2-[1S-(4-(Ethoxycarbonyl)piperazin-1-yl)carbonyl-3-(1,1-dimethylethoxycarbonyl)propyl]aminocarbonyl-7-methyl-4-(3-methoxycarbonyl)phenoxyquinoline (200 mg, 0.3 mmol) was dissolved in a mixture of methylene chloride and trifluoroacetic acid (5 mL, 4:1 mixture) and stirred for 3 hours. The solution was evaporated to an oil and dissolved in MeOH (10 mL). Lithium hydroxide (3 mL, 0.25 M) was added and the solution was stirred overnight. The reaction was evaporated, adjusted to pH <7 with TFA and purified by preparative HPLC to afford 2-[1S-(4-(ethoxycarbonyl)piperazin-1-yl)carbonyl-3-carboxypropyl]aminocarbonyl-7-methyl-4-(3-carboxy)phenoxyquinoline in trifluoroacetic acid, (25 mg, 15%). 1H NMR: (DMSO-d$_6$) 1.15 (t, 3), 1.80 (m, 1), 2.00 (m, 1), 2.55 (s, 3), 3.30–3.60 (m, 8), 4.05 (q), 4.95 (m, 1), 7.05 (s, 1), 7.61 (m, 2), 7.65 (d, 1), 7.75 (s, 1), 8.25 (d. 1), 8.91 (d, 2) ppm.

C. In a similar manner, the following compounds of formula (Ic) were prepared: 2-[1S-(4-(ethoxycarbonyl)piperazin-1-yl)carbonyl-3-carboxypropyl]aminocarbonyl-4-(3-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(2-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(2-amino-5-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(4-carboxy)phenoxyquinoline in 2,2,2-trifluoro-1,1-ethanediol;

2-[1S-(4-(ethoxycarbonyl)piperazin-1-yl)carbonyl-3-carboxypropyl]aminocarbonyl-4-(3-carboxymethyl)phenoxyquinoline in trifluoroacetic acid;

2-[1S-(4-(ethoxycarbonyl)piperazin-1-yl)carbonyl-3-carboxypropyl]aminocarbonyl-4-(3-(1-amino-1-carboxy)methyl)phenoxyquinoline in trifluoroacetic acid;

2-[1S-(4-(ethoxycarbonyl)piperazin-1-yl)carbonyl-3-carboxypropyl]aminocarbonyl-4-(3-(2-amino-2-carboxy)ethyl)phenoxyquinoline in trifluoroacetic acid;

2-[1S-(4-(ethoxycarbonyl)piperazin-1-yl)carbonyl-3-carboxypropyl]aminocarbonyl-4-(2-methyl-5-carboxy)phenoxyquinoline in trifluoroacetic acid;

2-[1S-(4-(ethoxycarbonyl)piperazin-1-yl)carbonyl-3-carboxypropyl]aminocarbonyl-4-(5-carboxy-2-diethylaminomethyl)phenoxyquinoline in trifluoroacetic acid;

2-[1S-(4-(ethoxycarbonyl)piperazin-1-yl)carbonyl-3-carboxypropyl]aminocarbonyl-4-(3-tetrazol-5-yl)phenoxyquinoline in 2,2,2-trifluoro-1,1-ethanediol; and 2-[1S-(4-(ethoxycarbonyl)piperazin-1-yl)carbonyl-3-carboxypropyl]aminocarbonyl-4-(3-trifluoromethylsulfonylamino)phenoxyquinoline in trifluoroacetic acid.

D. A solution of 2-[1S-(4-(ethoxycarbonyl)piperazin-1-yl)carbonyl-3-(methoxycarbonyl)propyl]aminocarbonyl-4-chloroquinoline (0.15 g, 0.313 mmol) and 1,2,3,4-tetrahydroisoquinoline (0.15 mmol) was mixed in 3 mL of DMSO and heated to 100° C. for 18 hours. The reaction was purified by reversed-phase HPLC. The product was dissolved in 0.25 M LiOH solution and stirred for 6 hours. Purification by reversed-phase HPLC afforded. 2-[1S-(4-(ethoxycarbonyl)piperazin-1-yl)carbonyl-3-carboxypropyl]aminocarbonyl-4-(1,2,3,4-tetrahydroisoquinolin-2-yl)quinoline in trifluoroacetic acid, to form a compound of formula (Id).

E. In a similar manner, other compounds of formula (Id) were prepared.

F. A solution of 2-[1S-(4-(ethoxycarbonyl)piperazin-1-yl)carbonyl-3-(1,1-dimethylethoxycarbonyl)propyl]aminocarbonyl-7-methyl-4-bromoquinoline (10 mg, 0.17 mmol), 3-carboxyphenylboronic acid (0.26 mmol), Pd(PPh$_3$) (40 mg), and 2 M sodium carbonate (217 µL) was combined in 10 mL of toluene-ethanol and heated at 80° C. overnight. The reaction was purified by reversed-phase HPLC. The product was dissolved in 10 mL of 1/1 TFA-methylene chloride solution and stirred for 2 hours. The product was concentrated in vacuo to afford 2-[1S-(4-(ethoxycarbonyl)piperazin-1-yl)carbonyl-3-carboxypropyl]aminocarbonyl-4-(3-carboxy)phenylquinoline in trifluoroacetic acid.

G. In a similar manner, other compounds of formula (Ie) were prepared.

EXAMPLE 4

Receptor Binding Studies

The ability of the compounds of the invention to bind to the platelet adenosine diphosphate ("ADP") receptor was tested using human washed platelets and rat washed platelets by displacement assays.

Methods:

One day old platelet concentrates were purchased from a local blood bank. The platelet concentrates were spun at 680 g for 10 minutes and the resulting pellets were resuspended in modified Tyrode's buffer (135 mM NaCl, 3.6 mL KCl, 1.8 mM MgCl$_2$, 9 mM HEPES, 0.18 mg/mL BSA, 4.5 mM glucose, pH 6.6) supplemented by 2% acid citrate dextrose (ACD). This platelet suspension was spun at 680 g for 10 minutes and the final pellet was resuspended in platelet binding buffer (20 mM Tris buffer, pH 7.5, 140 mM NaCl, 4 mM KCl, 2 mM MgCl$_2$, 1 mM EDTA, 0.1% BSA, 5 mM glucose, 2 µg/mL aprotinin, and 2 µg/mL leupeptin).

Platelets were isolated from rat whole blood as described in Example 13 with the final pellet resuspended in platelet binding buffer. The platelet number for binding to rat platelets (5×10$^6$ per well) was normalized to the number of platelets for binding to human platelet (4–6×10$^6$ per well).

Binding reactions were initiated by mixing [$^{33}$P]-2-methylthio-ADP (0.3–0.5 nM), test compounds and washed platelets in 96-well plates. The reactions were kept at ambient temperature for 60 minutes under constant shaking and were stopped by fast-filtration onto 96-well, glass-fiber (GFC) filter plates followed by washing 5 times with ice-cold 50 mM Tris buffer (pH 7.5). The amount of [$^{33}$P]-2-methylthio-ADP bound to the filters was measured by scintillation counting. Non-specific binding was determined in the presence of 10 µM unlabelled 2-methylthio-ADP. Competition studies were done using a single concentration of [$^{33}$P]-2-methylthio-ADP (0.3 nM) and varying concentrations of test compounds.

Results:

The compounds of the invention, when tested in this assay, demonstrated their ability to inhibitor the binding of [$^{33}$P]-2-methylthio-ADP binding to the human platelet ADP receptor and the rat platelet ADP receptor.

EXAMPLE 5

ADP-Induced Aggregation in Vitro Studies

The compounds of the invention were evaluated as functional antagonists of the platelet ADP receptor using both human and rat washed platelets.

Methods:

Human venous blood was collected from healthy, drug-free volunteers into ⅙ volume 3.2% acid/citrate/dextrose. Whole blood from Nembutal-anesthetized rats was collected from the abdominal aorta into 1/10 volume 3.8% acid/citrate/dextrose. Platelet rich plasma (PRP) was prepared by centrifugation at 800 g for 3–4 successive 1.5-minute intervals, with removal of the PRP after each spin. Alternatively, some PRP preps were performed by centrifugation at 100 g for 15 minutes. Washed platelets were prepared from the PRP by centrifugation at 680 g for 15 minutes and the platelet pellet resuspended in Tyrode's buffer (137 mM NaCl, 2.7 mM KCl, 12 mM NaHCO$_2$, 0.42 mM NaH$_2$PO, 1 mM MgCl$_2$, 2 mM CaCl$_2$, 0.35% BSA, 5.5 mM glucose, 5 mM HEPES, pH 7.35 supplemented with f.c. 10% ACD solution. The platelets were washed a total of two times under these acidic conditions and the platelet pellet collected by centrifugation at 680 g for 15 minutes at ambient temperature. The final platelet pellet was resuspended at 2×10$^8$ platelets/mL in Tyrode's buffer containing 0.02 units/mL apyrase. This platelet suspension was kept at 37° C. for at least 30 minutes prior to studies.

Inhibition of ADP-induced aggregation was measured at 37° C. in a 4-channel aggregometer. The platelet suspension (0.5 mL) was stirred at 1200 rpm. Human fibrinogen (400 µg) was added at time zero for 1 minute followed by 2 minute pre-incubation in the presence or absence of antagonist. Platelet aggregation was induced with the addition of 10 or 31.6 µM ADP (submaximal response) in human platelets or 3 or 10 µM ADP (submaximal response) in rat and monitored for 5 minutes. ADP-induced aggregation was quantified by measuring increase in light transmission (% T) compared to Tyrode's buffer control. IC$_{50}$ values were determined using the 4-parameter equation.

Results:

The compounds of the invention, when tested in this assay, demonstrated the ability to inhibit ADP-induced platelet aggregation in vitro in human and rat washed platelets.

EXAMPLE 6

Efficacy Assay

Inhibition of thrombus formation by compounds of the invention was evaluated in the rat arterio-venous (A-V) shunt model.

Methods:

Male Sprague-Dawley rats (350–400 g, 10–18 per group) were anesthetized with Nembutal (65 mg/kg, i.p). The left carotid artery and the right jugular vein were each cannulated with a piece of PE-50 tubing (8 cm, siliconized). Fifty minutes after anesthesia, the arterial and venous catheters were connected (A-V shunt) by a piece of shunt tubing (Tygon S-50-HL, 6 cm) that contained a silk thread (6-0 silk suture, 10 cm) coated with collagen (Horm, 100 µg/ml). Blood was allowed to flow through the A-V shunt for 10 minutes. The amount of thrombus deposited on the silk thread was measured as dry weight (24 hours at ambient temperature). A compound of the invention (1, 3 and 10 mg/kg) (as the appropriate salt form) or vehicle (15% DMSO in saline, 1 mL/kg) was injected via the jugular vein catheter 5 minutes before the A-V shunt. Blood samples (1 mL) were taken immediately before the dosing and at the end of the A-V shunt for measurements of ex vivo platelet aggregation and plasma levels of the compound of the invention.

Results:

When tested in this assay, compounds of the invention demonstrated the ability to dose-dependently inhibit platelet aggregation and thrombus formation in the rat A-V shunt model. Both the inhibition of platelet aggregation and thrombus formation were also parallel in relation to the changes in plasma drug concentrations. Thus, the inhibition of thrombus formation is correlated with the inhibition of platelet aggregation induced by the compound of the invention.

EXAMPLE 7

This example illustrates the preparation of representative pharmaceutical compositions for oral administration containing a compound of the invention, or a pharmaceutically acceptable salt thereof:

| A. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
|---|---|
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
|---|---|
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 8

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 9

This example illustrates the preparation of a representative pharmaceutical composition in suppository form containing a compound of the invention, or a pharmaceutically acceptable salt thereof:

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 10

This example illustrates the preparation of a representative pharmaceutical formulation for insufflation containing a compound of the invention, or a pharmaceutically acceptable salt thereof:

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

EXAMPLE 11

This example illustrates the preparation of a representative pharmaceutical formulation in nebulized form containing a compound of the invention, or a pharmaceutically acceptable salt thereof:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 12

This example illustrates the preparation of a representative pharmaceutical formulation in aerosol form containing a compound of the invention, or a pharmaceutically acceptable salt thereof:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula (II) or a pharmaceutically acceptable salt thereof:

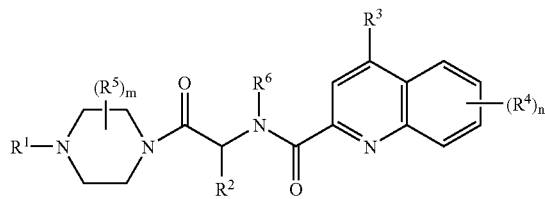

(II)

wherein:
m and n are independently 1 to 4;
$R^1$ is hydrogen, alkyl, carboxyalkyl, aryl, aralkyl, alkylcarbonyl, aryloxyalkylcarbonyl, carboxyalkylcarbonyl, alkoxycarbonylalkylcarbonyl, alkoxycarbonylalkyl, alkoxycarbonyl, arylcarbonyl, aryloxycarbonyl, aralkoxycarbonyl, cycloalkylcarbonyl, haloalkoxycarbonyl, aminocarbonyl, monoalkylaminocarbonyl, dialkylaminocarbonyl, alkoxycarbonylaminocarbonyl, or heterocyclylcarbonyl;
$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, or heterocyclylalkyl;
$R^3$ is heteroaryl optionally substituted by one or more substituents selected from the group consisting of alkyl, halo, haloalkyl, cyano, nitro, tetrazolyl, —$R^8$—$OR^7$, —$R^8$—$C(O)OR^7$, —$R^8$—$C(O)N(R^7)_2$, —$R^8$—$C(O)R^7$, —$R^8$—$N(R^7)_2$, —$R^6$—$N(R^7)C(O)R^7$, —$R^8$—$N(R^7)C(O)OR^9$, —$R^8$—$N(R^7)$—$S(O)_2$—$R^7$, and —$R^8$—$C[N(R^7)_2]C(O)OR^7$;
or $R^3$ is heteroarylalkoxy, wherein the alkoxy radical in the heteroarylalkoxy substituent is optionally substituted by one or more substituents selected from the group consisting of halo, cyano, nitro, —R—$OR^7$, —$R^8$—$C(O)OR^7$, —$R^8$—$C(O)N(R^7)_2$, —$R^8$—$C(O)R^7$, —$R^8$—$N(R^7)_2$, —$R^8$—$N(R^7)C(O)R^7$, and —$R^9$—$N(R^7)C(O)OR^9$), and wherein the heteroaryl radical in the heteroarylalkoxy substituent is independently optionally substituted by one or more substituents selected from the group consisting of alkyl, halo, haloalkyl, cyano, nitro, tetrazolyl, —$R^8$—$OR^7$, —$R^8$—C(O)$OR^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N($R^7$)C(O)$OR^8$, —$R^8$—N($R^7$)S(O)$_2R^7$, and —$R^8$—C[N($R^7$)$_2$]—C(O)$OR^7$;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^6$ is hydrogen, alkyl, carboxyalkyl, or alkoxycarbonylalkyl;

each $R^7$ is hydrogen, alkyl, aryl, aralkyl, or haloalkyl;

each $R^8$ is a bond or a straight or branched alkylene chain; and each $R^9$ is hydrogen, alkyl, aralkyl or haloalkyl;

as a single stereoisomer, a mixture of individual stereoisomers, or a racemic mixture.

2. The compound of claim 1 wherein:
m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is heteroaryl optionally substituted by one or more substituents selected from the group consisting of alkyl, halo, haloalkyl, —$R^8$—$OR^7$, —$R^8$—C(O)$OR^7$, —$R^8$—C(O)N($R^7$)$_2$, and —$R^8$—N($R^7$)$_2$;
each $R^4$ is independently selected from the group consisting of hydrogen, alkyl, alkoxy, halo, haloalkyl, amino, monoalkylamino, or dialkylamino;
$R^5$ is hydrogen;
$R^6$ is hydrogen;
each $R^7$ is hydrogen, alkyl, aryl, aralkyl, or haloalkyl; and
each $R^8$ is a bond or a straight or branched alkylene chain.

3. The compound 2-[1S(4-(ethoxycarbonyl)piperazin-1-yl)carbonyl-3-carboxypropyl]aminocarbonyl-4-(1,2,3,4-tetrahydroisoquinolin-2-yl)quinoline in trifluoroacetic acid, according to claim 2.

4. The compound of claim 1 wherein:
m is 1;
n is 1 or 2;
$R^1$ is hydrogen, aryl, aralkyl, or alkoxycarbonyl;
$R^2$ is hydrogen, carboxyalkyl, alkoxycarbonylalkyl or aralkoxycarbonylalkyl;
$R^3$ is heteroarylalkoxy, wherein the alkoxy radical in the heteroarylalkoxy substituent is optionally substituted by one or more substituents selected from the group consisting of halo and —$R^8$—C(O)$OR^7$, and wherein the heteroaryl radical in the heteroarylalkoxy substituent is independently optionally substituted by one or more substituents selected from the group consisting of alkyl, halo, haloalkyl, —$R^8$—$OR^7$, —$R^8$—C(O)$OR^7$, —$R^8$—C(O)N($R^7$)$_2$, and —$R^8$—N($R^7$)$_2$;
each $R^4$ is independently selected from the group consisting of hydrogen, alkyl, alkoxy, halo, haloalkyl, amino, monoalkylamino, or dialkylamino;
$R^5$ is hydrogen;

$R^6$ is hydrogen;
each $R^7$ is hydrogen, alkyl, aryl, aralkyl, or haloalkyl; and
each $R^8$ is a bond or a straight or branched alkylene chain.

5. The compound of claim 4 selected from the group consisting of the following:
2-[1S-(4-(ethoxycarbonyl)piperazin-1-yl)carbonyl-3-carboxypropyl]aminocarbonyl-4-(5-methylisoxazol-3-yl)methoxyquinoline in trifluoroacetic acid;
2-[1S-(4-(ethoxycarbonyl)piperazin-1-yl)carbonyl-3-carboxypropyl]aminocarbonyl-4-(2-methylthiazol-4-yl)methoxyquinoline in trifluoroacetic acetic acid;
2-[1-(4-(ethoxycarbonyl)piperazin-1-yl)carbonyl-3-carboxypropyl]aminocarbonyl-7-methyl-6-fluoro-4-(1-carboxy-1-thien-3-yl)methoxyquinoline in trifluoroacetic acid;
2-[1S-(4-(ethoxycarbonyl)piperazin-1-yl)carbonyl-3-carboxypropyl]aminocarbonyl-6-chloro-7-methyl-4-(5-methylisoxazol-3-yl)methoxyquinoline; and
2-[1-(4-(ethoxycarbonyl)piperazin-1-yl)carbonyl-3-carboxypropyl]aminocarbonyl-6-chloro-7-methyl-4-(2-methylthiazol-4-yl)methoxyquinoline in trifluoroacetic acid.

6. A pharmaceutical composition useful in treating a mammal having a disease-state characterized by thrombotic activity, which composition comprises a pharmaceutically acceptable excipient and a compound of formula (II) or a pharmaceutically acceptable salt thereof:

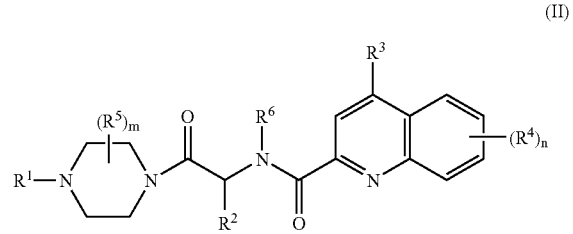

wherein:
m and n are independently 1 to 4;
$R^1$ is hydrogen, alkyl, carboxyalkyl, aryl, aralkyl, alkylcarbonyl, aryloxyalkylcarbonyl, carboxyalkylcarbonyl, alkoxycarbonylalkylcarbonyl, alkoxycarbonylalkyl, alkoxycarbonyl, arylcarbonyl, aryloxycarbonyl, aralkoxycarbonyl, cycloalkylcarbonyl, haloalkoxycarbonyl, aminocarbonyl, monoalkylaminocarbonyl, dialkylaminocarbonyl, alkoxycarbonylaminocarbonyl, or heterocyclylcarbonyl;
$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl) (alkyl)aminocarbonylalkyl, or heterocyclylalkyl;
$R^3$ is heteroaryl optionally substituted by one or more substituents selected from the group consisting of alkyl, halo, haloalkyl, cyano, nitro, tetrazolyl, —$R^8$—$OR^7$, —$R^8$—C(O)$OR^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N ($R^7$)C(O)O$R^9$, —$R^8$—N($R^7$)—S(O)$_2$—$R^7$, and —$R^8$—C[N($R^7$)$_2$]—C(O)O$R^7$;

or $R^3$ is heteroarylalkoxy, wherein the alkoxy radical in the heteroarylalkoxy substituent is optionally substituted by one or more substituents selected from the group consisting of halo, cyano, nitro, —$R^8$—O$R^7$, —$R^8$—C(O)O$R^7$, —$R^8$—C(O)N($R^7$)$_2$, —$R^8$—C(O)$R^7$, —$R^8$—N($R^7$)$_2$, —$R^8$—N($R^7$)C(O)$R^7$, and —$R^9$—N($R^7$)C(O)O$R^9$), and wherein the heteroaryl radical in the heteroarylalkoxy substituent is independently optionally substituted by one or more substituents selected from the group consisting of alkyl, halo, haloalkyl, cyano, nitro, tetrazolyl, —$R^8$—O$R^7$, —$R^8$—C(O)O$R^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N($R^7$)C(O)O$R^9$, R—N($R^7$)—S(O)$_2$—$R^7$, and —$R^8$—C[N($R^7$)$_2$]—C(O)O$R^7$;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^8$ is hydrogen, alkyl, carboxyalkyl, or alkoxycarbonylalkyl;

each $R^7$ is hydrogen, alkyl, aryl, aralkyl, or haloalkyl;

each $R^8$ is a bond or a straight or branched alkylene chain; and each $R^9$ is hydrogen, alkyl, aralkyl or haloalkyl;

as a single stereoisomer, a mixture of individual stereoisomers, or a racemic mixture.

7. A method of treating a disease-state characterized by thrombotic activity, which method comprises administering to a mammal having a disease-state characterized by thrombotic activity a therapeutically effective amount of a compound of formula (II) or a pharmaceutically acceptable salt thereof:

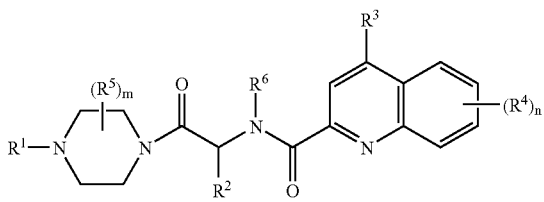

(II)

wherein:

m and n are independently 1 to 4;

$R^1$ is hydrogen, alkyl, carboxyalkyl, aryl, aralkyl, alkylcarbonyl, aryloxyalkylcarbonyl, carboxyalkylcarbonyl, alkoxycarbonylalkylcarbonyl, alkoxycarbonylalkyl, alkoxycarbonyl, aryloxycarbonyl, aryloxycarbonyl, aralkoxycarbonyl, cycloalkylcarbonyl, haloalkoxycarbonyl, aminocarbonyl, monoalkylaminocarbonyl, dialkylaminocarbonyl, alkoxycarbonylaminocarbonyl, or heterocyclylcarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, or heterocyclylalkyl;

$R^3$ is heteroaryl optionally substituted by one or more substituents selected from the group consisting of alkyl, halo, haloalkyl, cyano, nitro, tetrazolyl, —$R^8$—O$R^7$, —$R^8$—C(O)O$R^7$, —$R^8$—C(O)N($R^7$)$_2$, —$R^5$—C(O)$R^7$, —$R^8$—N($R^7$)$_2$, —$R^8$—N($R^7$)C(O)$R^7$, —$R^8$—N($R^7$)C(O)O$R^9$, —$R^8$—N($R^7$)—S(O)$_2$—$R^7$, and —$R^8$—C[N($R^7$)$_2$]—C(O)O$R^7$;

or $R^3$ is heteroarylalkoxy, wherein the alkoxy radical in the heteroarylalkoxy substituent is optionally substituted by one or more substituents selected from the group consisting of halo, cyano, nitro, —$R^8$—O$R^7$, —$R^8$—C(O)O$R^7$, —$R^8$—C(O)N($R^7$)$_2$, —$R^8$—C(O)$R^7$, —$R^8$—N($R^7$)$_2$, —$R^8$—N($R^7$)C(O)$R^7$, and —$R^9$—N($R^7$)C(O)O$R^9$), and wherein the heteroaryl radical in the heteroarylalkoxy substituent is independently optionally substituted by one or more substituents selected from the group consisting of alkyl, halo, haloalkyl, cyano, nitro, tetrazolyl, —$R^8$—O$R^7$, —$R^8$—C(O)O$R^7$, —$R^8$—C(O)N($R^7$)$_2$, —$R^8$—C(O)$R^7$, —$R^8$—N($R^7$)$_2$, —$R^8$—N($R^7$)C(O)$R^7$, —$R^8$—N($R^7$)C(O)O$R^9$, —$R^8$—N($R^7$)—S(O)$_2$—$R^7$, and —$R^8$—C[N($R^7$)$_2$]—C(O)O$R^7$;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R_8$ is hydrogen, alkyl, carboxyalkyl, or alkoxycarbonylalkyl;

each $R^7$ is hydrogen, alkyl, aryl, aralkyl, or haloalkyl;

each $R^8$ is a bond or a straight or branched alkylene chain; and each $R^9$ is hydrogen, alkyl, aralkyl or haloalkyl;

as a single stereoisomer, a mixture of individual stereoisomers, or a racemic mixture.

8. The pharmaceutical composition of claim 6 wherein:

m is 1;

n is 1 or 2;

$R^1$ is hydrogen, aryl, aralkyl, or alkoxycarbonyl;

$R^2$ is hydrogen, carboxyalkyl, alkoxycarbonylalkyl or aralkoxycarbonylalkyl;

$R_3$ is heteroaryl optionally substituted by one or more substituents selected from the group consisting of alkyl, halo, haloalkyl, —$R^8$—O$R^7$, —$R^8$—C(O)O$R^7$, —$R^8$—C(O)N($R^7$)$_2$, and —$R^8$—N($R^7$)$_2$;

each R⁴ is independently selected from the group consisting of hydrogen, alkyl, alkoxy, halo, haloalkyl, amino, monoalkylamino, or dialkylamino;
R⁵ is hydrogen;
R⁶ is hydrogen;
each R⁷ is hydrogen, alkyl, aryl, aralkyl, or haloalkyl; and
each R⁸ is a bond or a straight or branched alkylene chain.

9. The pharmaceutical composition of claim 8 wherein the compound is 2-[1S(4-(ethoxycarbonyl)piperazin-1-yl)carbonyl-3-carboxypropyl]aminocarbonyl-4-(1,2,3,4-tetrahydroisoquinolin-2-yl)quinoline in trifluoroacetic acid.

10. The pharmaceutical composition of claim 6 wherein:
m is 1;
n is 1 or 2;
R¹ is hydrogen, aryl, aralkyl, or alkoxycarbonyl;
R² is hydrogen, carboxyalkyl, alkoxycarbonylalkyl or aralkoxycarbonylalkyl;
R³ is heteroarylalkoxy, wherein the alkoxy radical in the heteroarylalkoxy substituent is optionally substituted by one or more substituents selected from the group consisting of halo and —R⁸—C(O)OR⁷, and wherein the heteroaryl radical in the heteroarylalkoxy substituent is independently optionally substituted by one or more substituents selected from the group consisting of alkyl, halo, haloalkyl, —R⁸—OR⁷, —R⁸—C(O)OR⁷, —R⁸—C(O)N(R⁷)₂, and —R⁸—N(R⁷)₂;
each R⁴ is independently selected from the group consisting of hydrogen, alkyl, alkoxy, halo, haloalkyl, amino, monoalkylamino, or dialkylamino;
R⁵ is hydrogen;
R⁶ is hydrogen;
each R⁷ is hydrogen, alkyl, aryl, aralkyl, or haloalkyl; and
each R⁸ is a bond or a straight or branched alkylene chain.

11. The pharmaceutical composition of claim 10 wherein the compound is selected from the group consisting of:
2-[1S-(4-(ethoxycarbonyl)piperazin-1-yl)carbonyl-3-carboxypropyl]aminocarbonyl-4-(5-methylisoxaxol-3-yl)methoxyquinoline in trifluoroacetic acid;
2-[1S-(4-(ethoxycarbonyl)piperazin-1-yl)carbonyl-3-carboxypropyl]aminocarbonyl-4-(2-methylthiazol-4-yl)methoxyquinoline in trifluoroacetic acid;
2-[1-(4-(ethoxycarbonyl)piperazin-1-yl)carbonyl-3-carboxypropyl]aminocarbonyl-7-methyl-6-fluoro-4-(1-carboxy-1-thien-3-yl)methoxyquinoline in trifluoroacetic acid;
2-[1S-(4-(ethoxycarbonyl)piperazin-1-yl)carbonyl-3-carboxypropyl]aminocarbonyl-6-chloro-7-methyl-4-(5-methylisoxazol-3-yl)methoxyquinoline; and
2-[1-(4-(ethoxycarbonyl)piperazin-1-yl)carbonyl-3-carboxypropyl]aminocarbonyl-6-chloro-7-methyl-4-(2-methylthiazol-4-yl)methoxyquinoline in trifluoroacetic acid.

12. The method of claim 7 wherein:
m is 1;
n is 1 or 2;
R¹ is hydrogen, aryl, aralkyl, or alkoxycarbonyl;
R² is hydrogen, carboxyalkyl, alkoxycarbonylalkyl or aralkoxycarbonylalkyl;
R³ is heteroaryl optionally substituted by one or more substituents selected from the group consisting of alkyl, halo, haloalkyl, —R⁸—OR⁷, —R⁸—C(O)OR⁷, —R⁸—C(O)N(R⁷)₂, and —R⁸—N(R⁷)₂;
each R⁴ is independently selected from the group consisting of hydrogen, alkyl, alkoxy, halo, haloalkyl, amino, monoalkylamino, or dialkylamino;
R⁵ is hydrogen;
R⁶ is hydrogen;
each R⁷ is hydrogen, alkyl, aryl, aralkyl, or haloalkyl; and
each R⁸ is a bond or a straight or branched alkylene chain.

13. The method of claim 12 wherein the compound is 2-[1S-(4-(ethoxycarbonyl)piperazin-1-yl)carbonyl-3-carboxypropyl]aminocarbonyl-4-(1,2,3,4-tetrahydroisoquinolin-2-yl)quinoline in trifluoroacetic acid.

14. The method of claim 7 wherein:
m is 1;
n is 1 or 2;
R¹ is hydrogen, aryl, aralkyl, or alkoxycarbonyl;
R² is hydrogen, carboxyalkyl, alkoxycarbonylalkyl or aralkoxycarbonylalkyl;
R³ is heteroarylalkoxy, wherein the alkoxy radical in the heteroarylalkoxy substituent is optionally substituted by one or more substituents selected from the group consisting of halo and —R⁸—C(O)OR⁷, and wherein the heteroaryl radical in the heteroarylalkoxy substituent is independently optionally substituted by one or more substituents selected from the group consisting of alkyl, halo, haloalkyl, —R⁸—OR⁷, —R⁸—C(O)OR⁷, —R⁸—C(O)N(R⁷)₂, and —R⁸—N(R⁷)₂;
each R⁴ is independently selected from the group consisting of hydrogen, alkyl, alkoxy, halo, haloalkyl, amino, monoalkylamino, or dialkylamino;
R⁵ is hydrogen;
R⁶ is hydrogen;
each R⁷ is hydrogen, alkyl, aryl, aralkyl, or haloalkyl; and
each R⁸ is a bond or a straight or branched alkylene chain.

15. The method of claim 14 wherein the compound is selected from the group consisting of:
2-[1S-(4-(ethoxycarbonyl)piperazin-1-yl)carbonyl-3-carboxypropyl]aminocarbonyl-4-(5-methylisoxaxol-3-yl)methoxyquinoline in trifluoroacetic acid;
2-[1S-(4-(ethoxycarbonyl)piperazin-1-yl)carbonyl-3-carboxypropyl]aminocarbonyl-4-(2-methylthiazol-4-yl)methoxyquinoline in trifluoroacetic acid;
2-[1-(4-(ethoxycarbonyl)piperazin-1-yl)carbonyl-3-carboxypropyl]aminocarbonyl-7-methyl-6-fluoro-4(1-carboxy-1-thien-3-yl)methoxyquinoline in trifluoroacetic acid;
2-[1S-(4-(ethoxycarbonyl)piperazin-1-yl)carbonyl-3-carboxypropyl]aminocarbonyl-6-chloro-7-methyl-4-(5-methylisoxazol-3-yl)methoxyquinoline; and
2-[1-(4-(ethoxycarbonyl)piperazin-1-yl)carbonyl-3-carboxypropyl]aminocarbonyl-6-chloro-7-methyl-4-(2-methylthiazol-4-yl)methoxyquinoline in trifluoroacetic acid.

* * * * *